United States Patent
Peliks et al.

(10) Patent No.: US 12,295,556 B2
(45) Date of Patent: May 13, 2025

(54) ROTATION BIOPSY SYSTEM AND HANDLE

(71) Applicant: Merit Medical Systems, Inc., South Jordan, UT (US)

(72) Inventors: Robert Bilgor Peliks, San Francisco, CA (US); Nathan Retzlaff, Kenosha, WI (US)

(73) Assignee: Merit Medical Systems, Inc., South Jordan, UT (US)

( * ) Notice: Subject to any disclaimer, the term of this patent is extended or adjusted under 35 U.S.C. 154(b) by 516 days.

(21) Appl. No.: 17/032,869

(22) Filed: Sep. 25, 2020

(65) Prior Publication Data

US 2021/0093305 A1    Apr. 1, 2021

Related U.S. Application Data

(60) Provisional application No. 62/907,135, filed on Sep. 27, 2019.

(51) Int. Cl.
*A61B 10/02* (2006.01)
*A61B 17/34* (2006.01)
*A61B 90/30* (2016.01)

(52) U.S. Cl.
CPC ...... *A61B 10/0275* (2013.01); *A61B 17/3421* (2013.01); *A61B 90/30* (2016.02); *A61B 2017/3409* (2013.01)

(58) Field of Classification Search
CPC . A61B 10/0275; A61B 90/30; A61B 17/3421; A61B 2017/3409; A61B 10/00–06; A61B 90/00; A61B 90/11; A61B 17/34; A61B 10/66; A61B 10/0283; A61B 10/0291; A61B 17/3205–32053; A61B 2010/045; A61B 2017/320064

See application file for complete search history.

(56) References Cited

U.S. PATENT DOCUMENTS

| | | | |
|---|---|---|---|
| 737,293 | A | 8/1903 | Summerfeldt |
| 1,585,934 | A | 12/1923 | Muir |
| 1,663,761 | A | 2/1927 | Johnson |
| D149,464 | S | 5/1948 | Adler |
| 2,850,007 | A | 9/1958 | Lingley |
| 2,953,934 | A | 9/1960 | Sundt |

(Continued)

FOREIGN PATENT DOCUMENTS

| | | | | |
|---|---|---|---|---|
| CA | 2589569 A1 | * | 11/2007 | ......... A61B 10/0041 |
| CA | 2683108 A1 | * | 4/2010 | ......... A61B 10/0275 |

(Continued)

OTHER PUBLICATIONS

Machine Translation of DE-202009003224, Patent Translation, pp. 1-19, printed on Jan. 7, 2023 (Year: 2009).*

(Continued)

*Primary Examiner* — Daniel L Cerioni
*Assistant Examiner* — Om Patel
(74) *Attorney, Agent, or Firm* — Dorsey & Whitney LLP

(57) ABSTRACT

Tools used to acquire a core tissue sample are disclosed. A portion of the tools may be configured to rotate when acquiring the core tissue sample. The tools include a partoff tab to sever the core tissue sample from a lesion and to retain the core tissue sample when the tool is removed from the patient. The tools may further include a light source to illuminate a working field.

17 Claims, 9 Drawing Sheets

(56) References Cited

U.S. PATENT DOCUMENTS

| | | |
|---|---|---|
| 3,001,522 A | 9/1961 | Irving |
| 3,019,733 A | 2/1962 | Braid |
| 3,224,434 A | 12/1965 | Molomut et al. |
| 3,477,423 A | 11/1969 | Griffith |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,628,524 A | 12/1971 | Jamshidi |
| 3,630,192 A | 12/1971 | Jamshidi |
| 3,727,602 A | 4/1973 | Hayden et al. |
| 3,732,858 A | 5/1973 | Banko |
| 3,800,783 A | 4/1974 | Jamshidi |
| 3,844,272 A | 10/1974 | Banko |
| 3,882,849 A | 5/1975 | Jamshidi |
| 3,929,123 A | 12/1975 | Jamshidi |
| 4,010,737 A | 3/1977 | Vilaghy |
| 4,256,119 A | 3/1981 | Gauthier |
| 4,258,722 A | 3/1981 | Sessions et al. |
| 4,266,555 A | 5/1981 | Jamshidi |
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,366,822 A | 1/1983 | Altshuler |
| 4,378,810 A | 4/1983 | Ishizaki et al. |
| 4,445,509 A | 5/1984 | Auth |
| 4,469,109 A | 9/1984 | Mehl |
| 4,487,209 A | 12/1984 | Mehl |
| 4,490,137 A | 12/1984 | Moukheibir |
| 4,513,754 A | 4/1985 | Lee |
| 4,549,554 A | 10/1985 | Markham |
| 4,557,265 A | 12/1985 | Anderson |
| 4,577,629 A | 3/1986 | Martinez |
| 4,589,414 A | 5/1986 | Yoshida et al. |
| 4,598,710 A | 7/1986 | Kleinberg et al. |
| 4,603,694 A | 8/1986 | Wheeler |
| 4,605,011 A | 8/1986 | Naslund |
| 4,617,430 A | 10/1986 | Bryant |
| 4,620,539 A | 11/1986 | Andrews et al. |
| 4,640,296 A | 2/1987 | Schnepp-Pesch |
| 4,643,197 A | 2/1987 | Greene et al. |
| 4,644,308 A | 2/1987 | Guery et al. |
| 4,645,153 A | 2/1987 | Granzow et al. |
| 4,655,226 A | 4/1987 | Lee |
| 4,662,869 A | 5/1987 | Wright |
| 4,678,459 A | 7/1987 | Onik et al. |
| 4,683,885 A | 8/1987 | Hutterer et al. |
| 4,696,298 A | 9/1987 | Higgins et al. |
| 4,702,260 A | 10/1987 | Wang |
| 4,708,147 A | 11/1987 | Haaga |
| 4,776,346 A | 10/1988 | Beraha et al. |
| 4,798,213 A | 1/1989 | Doppelt |
| 4,838,282 A | 6/1989 | Strasser et al. |
| 4,844,087 A | 7/1989 | Garg |
| 4,850,354 A | 7/1989 | McGurk-Burleson et al. |
| 4,893,635 A | 1/1990 | De Groot et al. |
| 4,907,598 A | 3/1990 | Bauer |
| 4,922,602 A | 5/1990 | Mehl |
| RE33,258 E | 7/1990 | Onik et al. |
| 4,940,061 A | 7/1990 | Terwilliger et al. |
| 4,952,817 A | 8/1990 | Bolan et al. |
| 4,958,625 A | 9/1990 | Bates et al. |
| 4,967,752 A | 11/1990 | Blumenthal et al. |
| 4,967,762 A | 11/1990 | Devries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,040,542 A | 8/1991 | Gray |
| 5,125,413 A | 6/1992 | Baran |
| 5,138,245 A | 8/1992 | Mattinger et al. |
| 5,146,921 A | 9/1992 | Terwilliger et al. |
| 5,158,528 A | 10/1992 | Walker et al. |
| 5,176,628 A | 1/1993 | Charles et al. |
| 5,197,482 A | 3/1993 | Rank et al. |
| 5,203,866 A | 4/1993 | Islam |
| 5,225,763 A | 7/1993 | Krohn et al. |
| 5,226,910 A | 7/1993 | Kajiyama et al. |
| 5,234,000 A | 8/1993 | Hakky et al. |
| 5,234,426 A | 8/1993 | Rank et al. |
| 5,236,334 A | 8/1993 | Bennett |
| 5,249,583 A | 10/1993 | Mallaby |
| 5,251,641 A | 10/1993 | Xavier |
| 5,257,632 A | 11/1993 | Turkel et al. |
| 5,269,791 A | 12/1993 | Mayzels et al. |
| 5,279,306 A | 1/1994 | Mehl |
| 5,282,476 A | 2/1994 | Terwilliger |
| 5,282,477 A | 2/1994 | Bauer |
| 5,284,472 A | 2/1994 | Sussman et al. |
| 5,292,327 A | 3/1994 | Dodd et al. |
| 5,324,306 A | 6/1994 | Makower et al. |
| 5,331,972 A | 7/1994 | Wadhwani et al. |
| 5,334,183 A | 8/1994 | Wuchinich |
| 5,336,229 A | 8/1994 | Noda |
| 5,357,974 A | 10/1994 | Baldridge |
| 5,368,029 A | 11/1994 | Holcombe et al. |
| 5,368,045 A | 11/1994 | Clement et al. |
| 5,395,313 A | 3/1995 | Naves et al. |
| 5,400,798 A | 3/1995 | Baran |
| 5,409,013 A | 4/1995 | Clement |
| 5,439,474 A | 8/1995 | Li |
| 5,441,510 A | 8/1995 | Simpson et al. |
| 5,456,267 A | 10/1995 | Stark |
| 5,458,112 A | 10/1995 | Weaver |
| 5,469,860 A | 11/1995 | De Santis |
| 5,479,486 A | 12/1995 | Saji |
| 5,485,917 A | 1/1996 | Early |
| 5,492,130 A | 2/1996 | Chiou |
| 5,505,210 A | 4/1996 | Clement |
| 5,511,556 A | 4/1996 | De Santis |
| 5,526,821 A | 6/1996 | Jamshidi |
| 5,526,822 A | 6/1996 | Burbank et al. |
| 5,527,322 A | 6/1996 | Clement |
| 5,535,755 A | 7/1996 | Heske |
| 5,538,009 A | 7/1996 | Byrne et al. |
| 5,546,957 A | 8/1996 | Heske |
| 5,554,151 A | 9/1996 | Hinchliffe |
| 5,560,373 A | 10/1996 | De Santis |
| 5,562,685 A | 10/1996 | Mollenauer et al. |
| 5,564,436 A | 10/1996 | Hakky et al. |
| 5,569,035 A | 10/1996 | Balfour et al. |
| 5,569,277 A | 10/1996 | Evans et al. |
| 5,569,284 A | 10/1996 | Young et al. |
| 5,575,293 A | 11/1996 | Miller et al. |
| 5,578,030 A | 11/1996 | Levin |
| 5,582,616 A | 12/1996 | Bolduc et al. |
| 5,591,170 A | 1/1997 | Speivack et al. |
| 5,601,585 A | 2/1997 | Banik et al. |
| 5,602,449 A | 2/1997 | Krause et al. |
| 5,617,874 A | 4/1997 | Baran |
| 5,643,304 A | 7/1997 | Schechter et al. |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,669,394 A | 9/1997 | Bergey |
| 5,699,909 A | 12/1997 | Foster |
| 5,700,265 A | 12/1997 | Romano |
| 5,709,697 A | 1/1998 | Ratcliff et al. |
| 5,720,760 A | 2/1998 | Becker et al. |
| 5,735,264 A | 4/1998 | Siczek et al. |
| 5,752,923 A | 5/1998 | Terwilliger |
| 5,755,714 A | 5/1998 | Murphy-Chutorian |
| 5,758,655 A | 6/1998 | Como Rodriguez et al. |
| 5,766,135 A | 6/1998 | Terwilliger |
| 5,769,086 A | 6/1998 | Ritchart et al. |
| 5,769,795 A | 6/1998 | Terwilliger |
| 5,775,333 A | 7/1998 | Burbank et al. |
| 5,788,651 A | 8/1998 | Weilandt |
| 5,792,167 A | 8/1998 | Kablik et al. |
| 5,807,275 A | 9/1998 | Jamshidi |
| 5,807,282 A | 9/1998 | Fowler |

(56) References Cited

U.S. PATENT DOCUMENTS

| | | | |
|---|---|---|---|
| 5,810,826 A | 9/1998 | Ang et al. |
| 5,817,033 A | 10/1998 | De Santis et al. |
| 5,817,034 A | 10/1998 | Milliman et al. |
| 5,823,970 A | 10/1998 | Terwilliger |
| 5,827,305 A | 10/1998 | Gordon |
| 5,830,219 A | 11/1998 | Bird et al. |
| D403,405 S | 12/1998 | Terwilliger |
| 5,843,001 A | 12/1998 | Goldenberg |
| 5,857,982 A | 1/1999 | Milliman et al. |
| 5,879,365 A | 3/1999 | Whitfield et al. |
| 5,908,233 A | 6/1999 | Heskett et al. |
| 5,913,857 A | 6/1999 | Ritchart et al. |
| 5,916,198 A | 6/1999 | Dillow |
| 5,916,229 A | 6/1999 | Evans |
| 5,928,164 A | 7/1999 | Burbank et al. |
| 5,944,673 A | 8/1999 | Gregoire et al. |
| 5,951,490 A | 9/1999 | Fowler |
| 5,951,575 A | 9/1999 | Bolduc et al. |
| 5,964,716 A | 10/1999 | Gregoire et al. |
| 5,971,939 A | 10/1999 | De Santis et al. |
| 5,976,164 A | 11/1999 | Bencini et al. |
| 5,980,469 A | 11/1999 | Burbank et al. |
| 5,980,545 A | 11/1999 | Pacala et al. |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart et al. |
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |
| 6,027,458 A | 2/2000 | Janssens |
| 6,036,657 A | 3/2000 | Milliman et al. |
| 6,050,955 A | 4/2000 | Bryan et al. |
| 6,071,284 A | 6/2000 | Fox |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,128 A | 8/2000 | Andelin |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,152,918 A | 11/2000 | Padilla et al. |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,221,029 B1 | 4/2001 | Mathis et al. |
| 6,228,039 B1 | 5/2001 | Binmoeller |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,280,399 B1 | 8/2001 | Rossin et al. |
| 6,283,925 B1 | 9/2001 | Terwilliger |
| 6,302,852 B1 | 10/2001 | Fleming, III et al. |
| 6,312,394 B1 | 11/2001 | Fleming, III |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,340,351 B1 | 1/2002 | Goldenberg |
| 6,358,217 B1 | 3/2002 | Bourassa |
| 6,361,504 B1 | 3/2002 | Shin |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,436,054 B1 | 8/2002 | Viola et al. |
| 6,443,910 B1 | 9/2002 | Krueger et al. |
| 6,478,751 B1 | 11/2002 | Krueger et al. |
| 6,482,158 B2 | 11/2002 | Mault |
| 6,485,436 B1 | 11/2002 | Truckai et al. |
| 6,488,636 B2 | 12/2002 | Bryan et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,551,255 B2 | 4/2003 | Van Bladel et al. |
| 6,554,778 B1 | 4/2003 | Fleming, III |
| 6,554,779 B2 | 4/2003 | Viola et al. |
| 6,585,664 B2 | 7/2003 | Burdoff et al. |
| 6,585,694 B1 | 7/2003 | Smith et al. |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,712,773 B1 | 3/2004 | Viola |
| 6,712,774 B2 | 3/2004 | Voegele et al. |
| 6,730,043 B2 | 5/2004 | Krueger et al. |
| 6,752,768 B2 | 6/2004 | Burdorff et al. |
| 6,753,671 B1 | 6/2004 | Harvey |
| 6,758,824 B1 | 7/2004 | Miller et al. |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,875,183 B2 | 4/2005 | Cervi |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Horner et al. |
| 7,001,342 B2 | 2/2006 | Faciszewski |
| 7,025,732 B2 | 4/2006 | Thompson et al. |
| 7,033,324 B2 | 4/2006 | Giusti et al. |
| 7,048,694 B2 | 5/2006 | Mark et al. |
| D525,583 S | 7/2006 | Vu |
| 7,081,123 B2 | 7/2006 | Merboth et al. |
| 7,153,274 B2 | 12/2006 | Stephens et al. |
| 7,189,206 B2 | 3/2007 | Quick et al. |
| 7,189,207 B2 | 3/2007 | Viola |
| 7,201,722 B2 | 4/2007 | Krueger |
| 7,219,867 B2 | 5/2007 | Kalis et al. |
| 7,226,424 B2 | 6/2007 | Ritchart et al. |
| 7,252,641 B2 * | 8/2007 | Thompson ......... A61B 10/0275 600/568 |
| 7,276,032 B2 | 10/2007 | Hibner et al. |
| 7,311,673 B2 | 12/2007 | Mueller, Jr. et al. |
| 7,328,794 B2 | 2/2008 | Lubs et al. |
| 7,331,930 B2 | 2/2008 | Faciszewski |
| 7,347,829 B2 | 3/2008 | Mark et al. |
| 7,374,544 B2 | 5/2008 | Freeman et al. |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,432,813 B2 | 10/2008 | Postma |
| 7,452,364 B2 | 11/2008 | Schreiber et al. |
| 7,452,367 B2 | 11/2008 | Rassman et al. |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,648,466 B2 | 1/2010 | Stephens et al. |
| 7,670,299 B2 | 3/2010 | Beckman et al. |
| 7,670,328 B2 | 3/2010 | Miller |
| 7,699,850 B2 | 4/2010 | Miller |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |

(56) References Cited

U.S. PATENT DOCUMENTS

| | | |
|---|---|---|
| 7,740,597 B2 | 6/2010 | Cicenas et al. |
| 7,762,961 B2 | 7/2010 | Heske et al. |
| 7,811,260 B2 | 10/2010 | Miller et al. |
| 7,815,642 B2 | 10/2010 | Miller |
| 7,828,746 B2 | 11/2010 | Teague |
| 7,850,620 B2 | 12/2010 | Miller et al. |
| 7,854,706 B2 | 12/2010 | Hibner |
| 7,883,476 B2 | 2/2011 | Miller et al. |
| 7,899,528 B2 | 3/2011 | Miller |
| 7,951,089 B2 | 5/2011 | Miller |
| 7,988,643 B2 | 8/2011 | Hoffmann et al. |
| 8,002,733 B2 | 8/2011 | Kraft et al. |
| 8,038,664 B2 | 10/2011 | Miller |
| 8,070,689 B2 | 12/2011 | Masseglia et al. |
| 8,070,690 B2 | 12/2011 | Ikehara et al. |
| 8,142,365 B2 | 3/2012 | Miller |
| 8,187,203 B2 | 5/2012 | McClellan |
| 8,251,917 B2 | 8/2012 | Almazan |
| 8,308,693 B2 | 11/2012 | Miller et al. |
| 8,343,072 B2 | 1/2013 | Bacon et al. |
| 8,357,104 B2 | 1/2013 | Moos et al. |
| 8,419,683 B2 | 4/2013 | Miller et al. |
| 8,439,846 B2 | 5/2013 | Zambelli |
| 8,444,573 B2 | 5/2013 | Flatland |
| 8,465,491 B2 | 6/2013 | Yedicka et al. |
| 8,480,632 B2 | 7/2013 | Miller et al. |
| 8,506,568 B2 | 8/2013 | Miller |
| 8,617,085 B2 | 12/2013 | Moran, Jr. |
| 8,641,715 B2 | 2/2014 | Miller |
| 8,656,929 B2 | 2/2014 | Miller et al. |
| 8,668,698 B2 | 3/2014 | Miller et al. |
| 8,672,954 B2 | 3/2014 | Oren et al. |
| 8,684,978 B2 | 4/2014 | Miller et al. |
| 8,690,791 B2 | 4/2014 | Miller |
| 8,715,287 B2 | 5/2014 | Miller |
| 8,728,005 B2 | 5/2014 | McClellan |
| 8,728,006 B2 | 5/2014 | McClellan |
| 8,734,363 B2 | 5/2014 | Bacon |
| 8,812,101 B2 | 8/2014 | Miller et al. |
| 8,834,417 B2 | 9/2014 | Moos et al. |
| 8,845,621 B2 | 9/2014 | Fojtik |
| 8,870,872 B2 | 10/2014 | Miller |
| 8,876,826 B2 | 11/2014 | Miller |
| 8,944,069 B2 | 2/2015 | Miller et al. |
| 8,974,410 B2 | 3/2015 | Miller et al. |
| 8,992,535 B2 | 3/2015 | Miller |
| 8,998,848 B2 | 4/2015 | Miller et al. |
| 9,072,543 B2 | 7/2015 | Miller et al. |
| 9,078,637 B2 | 7/2015 | Miller |
| 9,226,732 B2 | 1/2016 | Azimpoor et al. |
| 9,237,906 B2 | 1/2016 | Janssens |
| 9,295,487 B2 | 3/2016 | Miller et al. |
| 9,314,228 B2 | 4/2016 | Miller |
| 9,314,270 B2 | 4/2016 | Miller |
| 9,332,970 B2 | 5/2016 | Beck et al. |
| 9,393,031 B2 | 7/2016 | Miller |
| 9,402,602 B2 | 8/2016 | Lee |
| 9,414,815 B2 | 8/2016 | Miller et al. |
| 9,433,400 B2 | 9/2016 | Miller |
| 9,439,667 B2 | 9/2016 | Miller |
| 9,451,968 B2 | 9/2016 | Miller et al. |
| 9,504,477 B2 | 11/2016 | Miller et al. |
| 9,510,910 B2 | 12/2016 | Miller et al. |
| 9,545,243 B2 | 1/2017 | Miller et al. |
| 9,572,551 B2 | 2/2017 | Fumex |
| 9,615,816 B2 | 4/2017 | Woodward |
| 9,717,564 B2 | 8/2017 | Miller et al. |
| 9,717,847 B2 | 8/2017 | Miller et al. |
| 9,730,729 B2 | 8/2017 | Kilcoin et al. |
| 9,839,740 B2 | 12/2017 | Beamer et al. |
| 9,872,703 B2 | 1/2018 | Miller et al. |
| 9,883,853 B2 | 2/2018 | Woodward et al. |
| 9,949,755 B2 | 4/2018 | Hanson |
| 10,016,216 B2 | 7/2018 | Sauter |
| 10,052,111 B2 | 8/2018 | Miller et al. |
| 10,064,630 B2 | 9/2018 | Forman et al. |
| 10,064,671 B2 | 9/2018 | Sharkey et al. |
| 10,092,320 B2 | 10/2018 | Morgan et al. |
| 10,130,343 B2 | 11/2018 | Miller et al. |
| 10,166,337 B2 | 1/2019 | Martz |
| 10,245,010 B2 | 4/2019 | Miller et al. |
| 10,258,783 B2 | 4/2019 | Miller et al. |
| 10,335,126 B2 | 7/2019 | Harrison et al. |
| 10,413,282 B2 | 9/2019 | Miller |
| 10,492,830 B2 | 12/2019 | Miller |
| 10,993,707 B2 | 5/2021 | McGillicuddy |
| 2001/0005778 A1 | 6/2001 | Ouchi |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0019596 A1* | 2/2002 | Eggers ............ A61B 18/1482 600/564 |
| 2002/0042581 A1 | 4/2002 | Cervi |
| 2002/0045840 A1 | 4/2002 | Voegele et al. |
| 2002/0065474 A1 | 5/2002 | Viola |
| 2002/0067151 A1 | 6/2002 | Tanishita |
| 2002/0068878 A1 | 6/2002 | Jasonni et al. |
| 2002/0077646 A1 | 6/2002 | Truwit et al. |
| 2002/0082518 A1 | 6/2002 | Weiss et al. |
| 2002/0107043 A1 | 8/2002 | Adamson et al. |
| 2002/0120212 A1 | 8/2002 | Ritchart et al. |
| 2002/0151822 A1 | 10/2002 | Brudorff et al. |
| 2002/0156395 A1 | 10/2002 | Stephens et al. |
| 2003/0078586 A1 | 4/2003 | Shapira |
| 2003/0114875 A1 | 6/2003 | Sjostrom |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0225344 A1 | 12/2003 | Miller |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0049128 A1 | 3/2004 | Miller et al. |
| 2004/0054299 A1 | 3/2004 | Burdorff et al. |
| 2004/0092992 A1 | 5/2004 | Adams et al. |
| 2004/0127814 A1 | 7/2004 | Negroni |
| 2004/0133124 A1 | 7/2004 | Bates et al. |
| 2004/0167427 A1 | 8/2004 | Quick et al. |
| 2004/0186393 A1 | 9/2004 | Leigh et al. |
| 2004/0215102 A1 | 10/2004 | Ikehara et al. |
| 2004/0215103 A1 | 10/2004 | Mueller et al. |
| 2004/0220495 A1 | 11/2004 | Cahir et al. |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0080355 A1 | 4/2005 | Mark |
| 2005/0085838 A1 | 4/2005 | Thompson et al. |
| 2005/0101879 A1 | 5/2005 | Shidham et al. |
| 2005/0113715 A1 | 5/2005 | Scwindt et al. |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0165328 A1 | 7/2005 | Heske et al. |
| 2005/0165404 A1 | 7/2005 | Miller |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0267383 A1 | 12/2005 | Groenke et al. |
| 2005/0275378 A1 | 12/2005 | Canino et al. |
| 2005/0277829 A1 | 12/2005 | Tsonton et al. |
| 2005/0277871 A1 | 12/2005 | Selis |

(56) References Cited

U.S. PATENT DOCUMENTS

| | | |
|---|---|---|
| 2006/0030784 A1 | 2/2006 | Miller et al. |
| 2006/0074344 A1 | 4/2006 | Hibner |
| 2006/0074345 A1 | 4/2006 | Hibner |
| 2006/0074346 A1 | 4/2006 | Hibner |
| 2006/0113958 A1 | 6/2006 | Lobert et al. |
| 2006/0116603 A1 | 6/2006 | Shibazaki et al. |
| 2006/0129063 A1 | 6/2006 | Thompson et al. |
| 2006/0173377 A1 | 8/2006 | McCullough et al. |
| 2006/0178666 A1 | 8/2006 | Cosman et al. |
| 2006/0184063 A1 | 8/2006 | Miller |
| 2006/0184188 A1 | 8/2006 | Li et al. |
| 2006/0241515 A1 | 10/2006 | Jones et al. |
| 2006/0258953 A1 | 11/2006 | Lee |
| 2006/0258956 A1 | 11/2006 | Haberstich et al. |
| 2007/0010843 A1 | 1/2007 | Green |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0066987 A1 | 3/2007 | Scanlan, Jr. |
| 2007/0073326 A1 | 3/2007 | Miller et al. |
| 2007/0090788 A1 | 4/2007 | Hansford et al. |
| 2007/0093841 A1 | 4/2007 | Hoogland |
| 2007/0106176 A1 | 5/2007 | Mark et al. |
| 2007/0118049 A1 | 5/2007 | Viola |
| 2007/0149894 A1 | 6/2007 | Heske et al. |
| 2007/0161925 A1 | 7/2007 | Quick et al. |
| 2007/0167782 A1 | 7/2007 | Callahan et al. |
| 2007/0179401 A1 | 8/2007 | Hibner |
| 2007/0213590 A1 | 9/2007 | Squicciarina |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0270710 A1 | 11/2007 | Frass et al. |
| 2007/0270712 A1 | 11/2007 | Wiksell et al. |
| 2007/0276288 A1 | 11/2007 | Khaw |
| 2007/0287933 A1 | 12/2007 | Phan et al. |
| 2007/0293788 A1 | 12/2007 | Entrekin et al. |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0045857 A1 | 2/2008 | Miller et al. |
| 2008/0045861 A1 | 2/2008 | Miller et al. |
| 2008/0045965 A1 | 2/2008 | Miller et al. |
| 2008/0064925 A1 | 3/2008 | Gill et al. |
| 2008/0064984 A1 | 3/2008 | Pflueger |
| 2008/0071193 A1 | 3/2008 | Reuber et al. |
| 2008/0079391 A1 | 4/2008 | Schroeck et al. |
| 2008/0110261 A1 | 5/2008 | Randall et al. |
| 2008/0135443 A1 | 6/2008 | Frojd et al. |
| 2008/0139961 A1 | 6/2008 | Slama et al. |
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1* | 7/2008 | Nicoson ............ A61B 10/0275 600/567 |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bichenbach |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0223904 A1 | 9/2008 | Marczyk |
| 2008/0228103 A1 | 9/2008 | Ritchie et al. |
| 2008/0228104 A1 | 9/2008 | Uber et al. |
| 2008/0232604 A1 | 9/2008 | Dufresne et al. |
| 2008/0234715 A1 | 9/2008 | Pescue et al. |
| 2008/0243163 A1 | 10/2008 | Masseglia |
| 2008/0262383 A1 | 10/2008 | Routhier et al. |
| 2008/0281225 A1 | 11/2008 | Spero et al. |
| 2008/0287826 A1 | 11/2008 | Videbaek et al. |
| 2008/0287859 A1 | 11/2008 | Miller et al. |
| 2008/0306404 A1 | 12/2008 | Ronald |
| 2008/0306405 A1 | 12/2008 | Masseglia et al. |
| 2008/0306406 A1 | 12/2008 | Thompson et al. |
| 2008/0308607 A1 | 12/2008 | Timm et al. |
| 2008/0312554 A1 | 12/2008 | Garrison |
| 2008/0319341 A1 | 12/2008 | Taylor et al. |
| 2009/0030405 A1 | 1/2009 | Quick et al. |
| 2009/0048533 A1 | 2/2009 | Miller |
| 2009/0062624 A1 | 3/2009 | Neville |
| 2009/0088666 A1 | 4/2009 | Miller et al. |
| 2009/0118641 A1 | 5/2009 | Van Dam et al. |
| 2009/0125062 A1 | 5/2009 | Arnin |
| 2009/0137927 A1 | 5/2009 | Miller |
| 2009/0171243 A1 | 7/2009 | Hibner et al. |
| 2009/0204021 A1 | 8/2009 | Shabaz et al. |
| 2009/0082695 A1 | 9/2009 | Whitehead |
| 2009/0227893 A1 | 9/2009 | Coonahan et al. |
| 2010/0030020 A1 | 2/2010 | Sanders et al. |
| 2010/0030105 A1 | 2/2010 | Noishiki et al. |
| 2010/0063416 A1 | 3/2010 | Cicenas et al. |
| 2010/0064393 A1 | 3/2010 | Berka et al. |
| 2010/0069790 A1 | 3/2010 | Green |
| 2010/0113972 A1* | 5/2010 | Alvarado ........... A61B 10/0266 600/567 |
| 2010/0152611 A1 | 6/2010 | Parihar et al. |
| 2010/0160820 A1 | 6/2010 | Weikel, Jr. et al. |
| 2010/0204649 A1 | 8/2010 | Miller et al. |
| 2010/0210966 A1 | 8/2010 | Videbaek |
| 2010/0234760 A1 | 9/2010 | Almazan |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2011/0071391 A1 | 3/2011 | Speeg |
| 2011/0082387 A1 | 4/2011 | Miller et al. |
| 2011/0152715 A1 | 6/2011 | Delap et al. |
| 2011/0160611 A1 | 6/2011 | Ritchart et al. |
| 2011/0224577 A1 | 9/2011 | Park |
| 2011/0313316 A1 | 12/2011 | Ranpura et al. |
| 2012/0109061 A1 | 5/2012 | Miller et al. |
| 2012/0116248 A1 | 5/2012 | McWeeney et al. |
| 2012/0130274 A1 | 5/2012 | Persat |
| 2012/0197157 A1 | 8/2012 | Ryan et al. |
| 2012/0253228 A1 | 10/2012 | Schembre et al. |
| 2013/0041345 A1 | 2/2013 | Kilcoin et al. |
| 2013/0096508 A1 | 4/2013 | Beamer et al. |
| 2013/0096561 A1 | 4/2013 | Miller et al. |
| 2013/0204160 A1 | 8/2013 | McKenna et al. |
| 2014/0100448 A1 | 4/2014 | Neilan |
| 2014/0207021 A1 | 7/2014 | Snow |
| 2014/0221870 A1 | 8/2014 | McClellan |
| 2014/0262408 A1 | 9/2014 | Woodard |
| 2014/0262880 A1 | 9/2014 | Yoon |
| 2014/0276205 A1 | 9/2014 | Miller et al. |
| 2014/0276206 A1 | 9/2014 | Woodward |
| 2014/0276839 A1 | 9/2014 | Forman et al. |
| 2014/0343454 A1 | 11/2014 | Miller et al. |
| 2015/0127006 A1 | 5/2015 | Miller |
| 2015/0129456 A1 | 5/2015 | Miller et al. |
| 2015/0223786 A1 | 8/2015 | Morgan et al. |
| 2015/0230823 A1 | 8/2015 | Morgan et al. |
| 2015/0351797 A1 | 12/2015 | Miller et al. |
| 2016/0022282 A1 | 1/2016 | Miller et al. |
| 2016/0030013 A1 | 2/2016 | Harrison, IV et al. |
| 2016/0030016 A1 | 2/2016 | McWeeney et al. |
| 2016/0058432 A1 | 3/2016 | Miller |
| 2016/0066954 A1 | 3/2016 | Miller et al. |
| 2016/0081678 A1 | 3/2016 | Kappel et al. |

(56) References Cited

U.S. PATENT DOCUMENTS

| | | | |
|---|---|---|---|
| 2016/0174950 A1 | 6/2016 | Rusnak |
| 2016/0183974 A1 | 6/2016 | Miller |
| 2016/0184509 A1 | 6/2016 | Miller et al. |
| 2016/0206346 A1 | 7/2016 | Miller |
| 2016/0317133 A1 | 11/2016 | Orts et al. |
| 2016/0354067 A1 | 12/2016 | Rohl et al. |
| 2016/0367287 A1 | 12/2016 | Fumex et al. |
| 2016/0367288 A1 | 12/2016 | Miller |
| 2016/0374722 A1 | 12/2016 | Miller |
| 2017/0007271 A1 | 1/2017 | Miller et al. |
| 2017/0035397 A1 | 2/2017 | Miller et al. |
| 2017/0056029 A1 | 3/2017 | Wolters et al. |
| 2017/0333011 A1 | 11/2017 | Peliks |
| 2017/0340401 A1 | 11/2017 | Miller et al. |
| 2018/0085144 A1 | 3/2018 | McGillicuddy |
| 2018/0092633 A1 | 4/2018 | Peliks |
| 2018/0125465 A1 | 5/2018 | Muse et al. |
| 2018/0256209 A1 | 9/2018 | Muse et al. |
| 2018/0333145 A1 | 11/2018 | Snow |
| 2018/0333146 A1 | 11/2018 | Hallisey et al. |
| 2018/0333147 A1 | 11/2018 | Snow et al. |
| 2019/0038345 A1 | 2/2019 | Pellegrino et al. |
| 2019/0090861 A1 | 3/2019 | Snow et al. |
| 2019/0117201 A1 | 4/2019 | Beck et al. |
| 2019/0142398 A1* | 5/2019 | Ranpura ......... A61B 10/0275 600/567 |
| 2019/0365360 A1 | 12/2019 | Vetter et al. |
| 2020/0197044 A1 | 6/2020 | Fayne et al. |
| 2020/0268362 A1 | 8/2020 | Van Liere et al. |
| 2021/0121201 A1 | 4/2021 | Tierney et al. |
| 2021/0177386 A1 | 6/2021 | Peliks et al. |
| 2021/0275154 A1 | 9/2021 | Peliks et al. |

FOREIGN PATENT DOCUMENTS

| | | | |
|---|---|---|---|
| CN | 107920808 | * 4/2018 | |
| DE | 2848314 | 10/1979 | |
| DE | 3924291 | 1/1991 | |
| DE | 4120329 | 1/1992 | |
| DE | 4041614 | 10/1992 | |
| DE | 2453058 | 5/1996 | |
| DE | 10034297 | 4/2001 | |
| DE | 10026303 | 2/2002 | |
| DE | 20209525 | 11/2002 | |
| DE | 10235480 | 2/2004 | |
| DE | 202009003224 | * 6/2009 | ......... A61B 10/0275 |
| EP | 0433717 | 6/1991 | |
| EP | 541377 | 5/1993 | |
| EP | 0890339 | 1/1999 | |
| EP | 0995400 | 4/2000 | |
| EP | 1074271 | 2/2001 | |
| EP | 1520518 | 4/2005 | |
| EP | 1579809 | 9/2005 | |
| EP | 1665958 | 6/2006 | |
| EP | 2095772 | 2/2009 | |
| EP | 2106750 | 10/2009 | |
| FR | 1345429 | 12/1963 | |
| FR | 2739293 | 4/1997 | |
| GB | 2018601 | 10/1979 | |
| GB | 2038640 | 12/1979 | |
| GB | 21300890 | 6/1984 | |
| JP | H10508504 | 8/1998 | |
| JP | 2005530554 | 10/2005 | |
| JP | 2006509545 | 3/2006 | |
| JP | 2006528907 | 12/2006 | |
| JP | 2007502159 | 2/2007 | |
| JP | 2007313332 | * 12/2007 | |
| RU | 2212848 | 11/2002 | |
| SU | 1454457 | 1/1989 | |
| WO | 199314700 | 8/1993 | |
| WO | 199416181 | 7/1994 | |
| WO | 199428801 | 12/1994 | |
| WO | 199628097 | 9/1996 | |
| WO | 199825522 | 6/1998 | |
| WO | 199831285 | 7/1998 | |
| WO | 199835615 | 8/1998 | |
| WO | 199846290 | 10/1998 | |
| WO | 199933501 | 7/1999 | |
| WO | 200004832 | 2/2000 | |
| WO | 200030546 | 6/2000 | |
| WO | 200059378 | 10/2000 | |
| WO | 200128439 | 4/2001 | |
| WO | 200172230 | 10/2001 | |
| WO | 2001078590 | 10/2001 | |
| WO | 200222023 | 3/2002 | |
| WO | 200232318 | 4/2002 | |
| WO | 2002069808 | 9/2002 | |
| WO | 2004075728 | 9/2004 | |
| WO | 2004082489 | 9/2004 | |
| WO | 20040757719 | 9/2004 | |
| WO | 2005013830 | 2/2005 | |
| WO | 2006015302 | 2/2006 | |
| WO | 2006061514 | 6/2006 | |
| WO | 2007047128 | 4/2007 | |
| WO | 2007095330 | 8/2007 | |
| WO | 2007112751 | 10/2007 | |
| WO | 2008021687 | 2/2008 | |
| WO | 2008024684 | 2/2008 | |
| WO | 2008040812 | 4/2008 | |
| WO | 2008131362 | 10/2008 | |
| WO | 2010107424 | 9/2010 | |
| WO | WO-2010138944 A2 * | 12/2010 | ............. A61B 10/02 |
| WO | 2014142948 | 9/2014 | |
| WO | WO-2016196536 A1 * | 12/2016 | ......... A61B 10/0266 |
| WO | 2017046531 | 3/2017 | |
| WO | 2019049098 | 3/2019 | |
| WO | 2010096139 | 8/2021 | |

OTHER PUBLICATIONS

Machine Translation of JP-2007313332, Patent Translate, pp. 1-29, printed on May 9, 2023 (Year: 2007).*
Machine Translation of CN 107920808, Patent Translate, pp. 1-33, printed on Feb. 16, 2024 (Year: 2018).*
Notice of Allowance dated Jul. 9, 2021 for U.S. Appl. No. 15/982,624.
Notice of Allowance dated Aug. 25, 2021 for U.S. Appl. No. 15/965,109.
International Search Report and Written Opinion dated Jan. 8, 2021 for PCT/US2020/052779.
International Search Report and Written Opinion dated Jul. 2, 2009 for PCT/KR2009/006741.
International Search Report and Written Opinion dated Sep. 4, 2018 for PCT/US2018/033188.
Office Action dated May 12, 2020 for U.S. Appl. No. 15/982,624.
Office Action dated May 12, 2020 for U.S. Appl. No. 15/982,777.
Office Action dated Jul. 1, 2020 for U.S. Appl. No. 15/980,116.
Office Action dated Nov. 17, 2020 for U.S. Appl. No. 15/982,624.
Office Action dated Nov. 27, 2020 for U.S. Appl. No. 15/982,777.
European Search Report dated Feb. 1, 2021 for EP18802126.5.
International Search Report and Written Opinion dated Apr. 7, 2021 for PCT/US2020/063934.
International Search Report and Written Opinion dated Jun. 23, 2021 for PCT/US2021/020599.
Office Action dated Dec. 12, 2023 for U.S. Appl. No. 17/116,294.
Office Action dated Apr. 26, 2024 for U.S. Appl. No. 17/116,294.
Notice of Allowance dated Aug. 2, 2024 for U.S. Appl. No. 17/116,294.

* cited by examiner

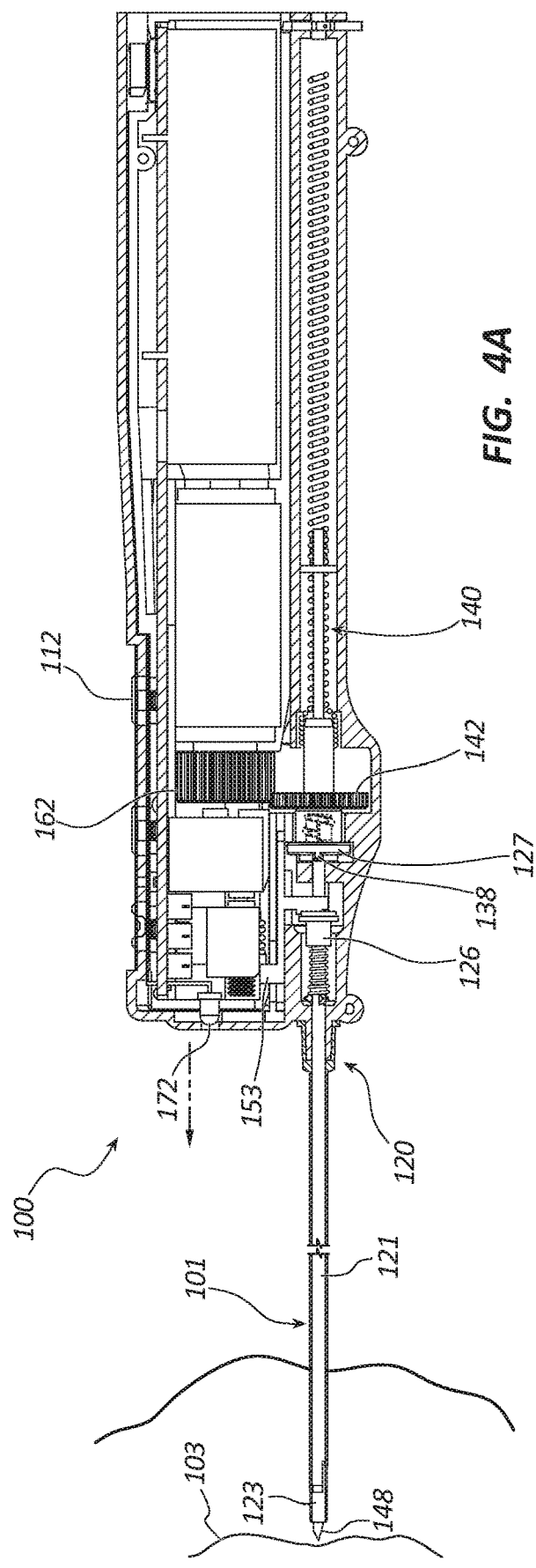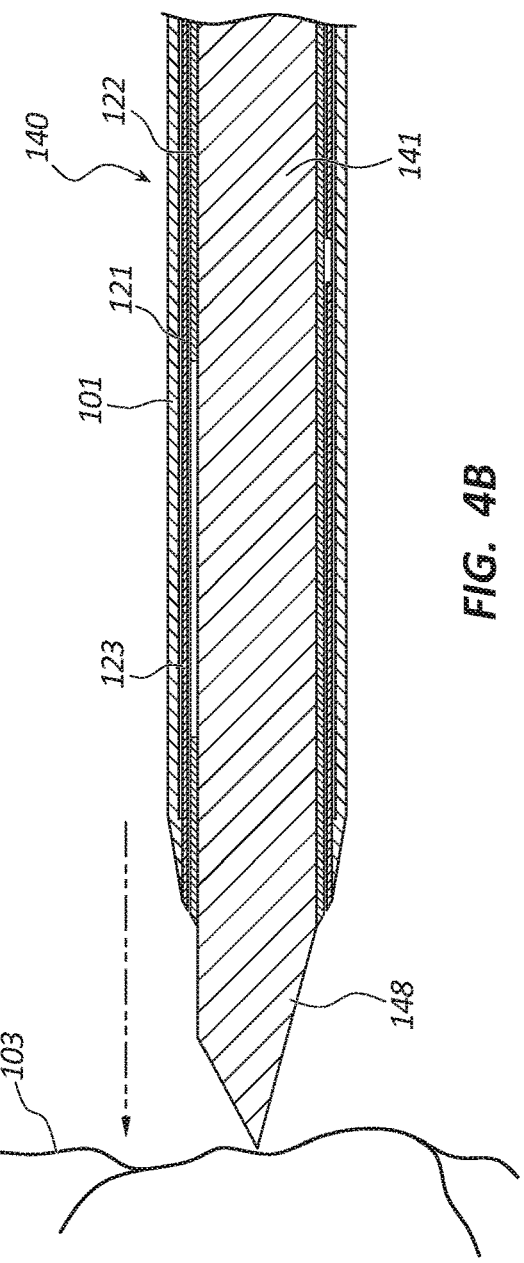
FIG. 4A
FIG. 4B

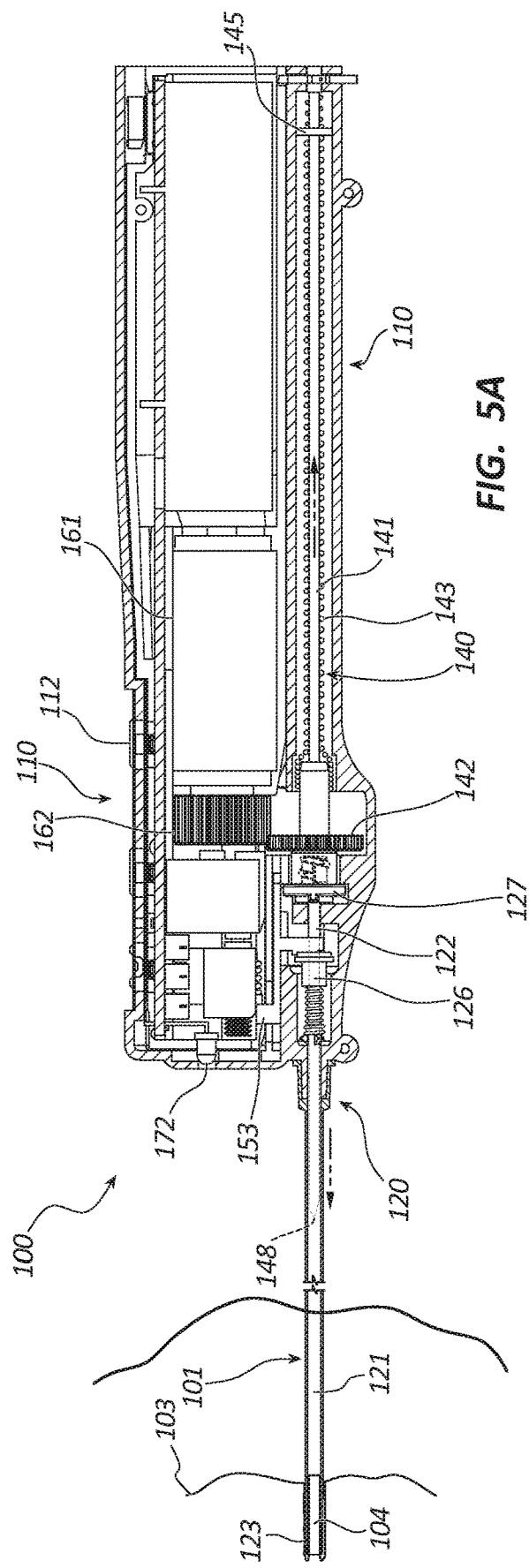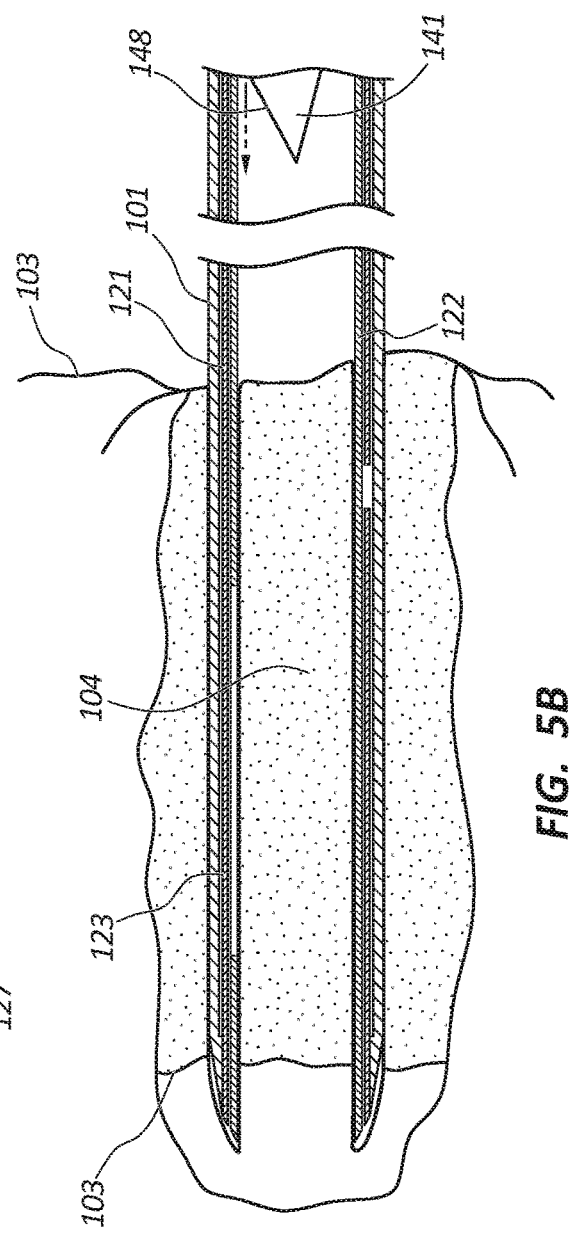
FIG. 5A
FIG. 5B

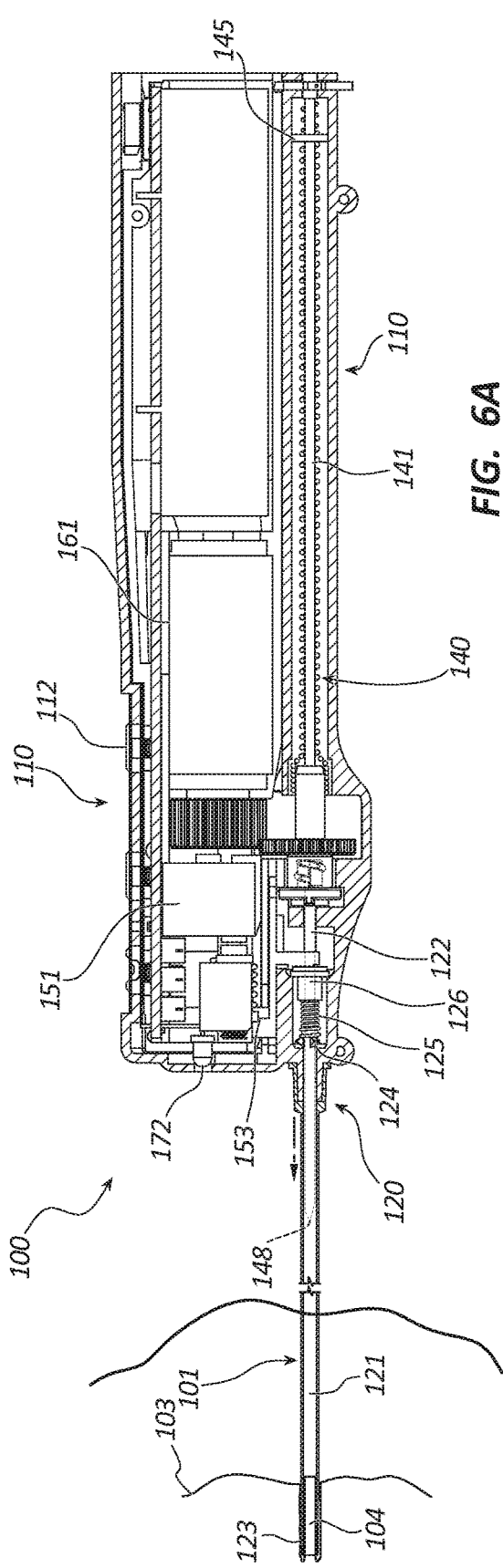
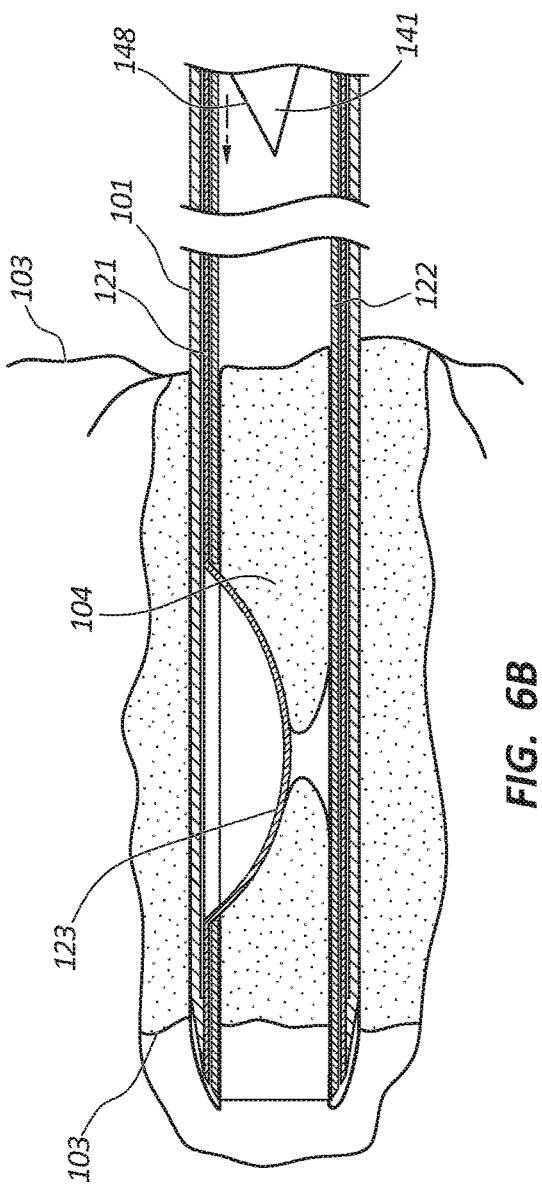
FIG. 6A
FIG. 6B

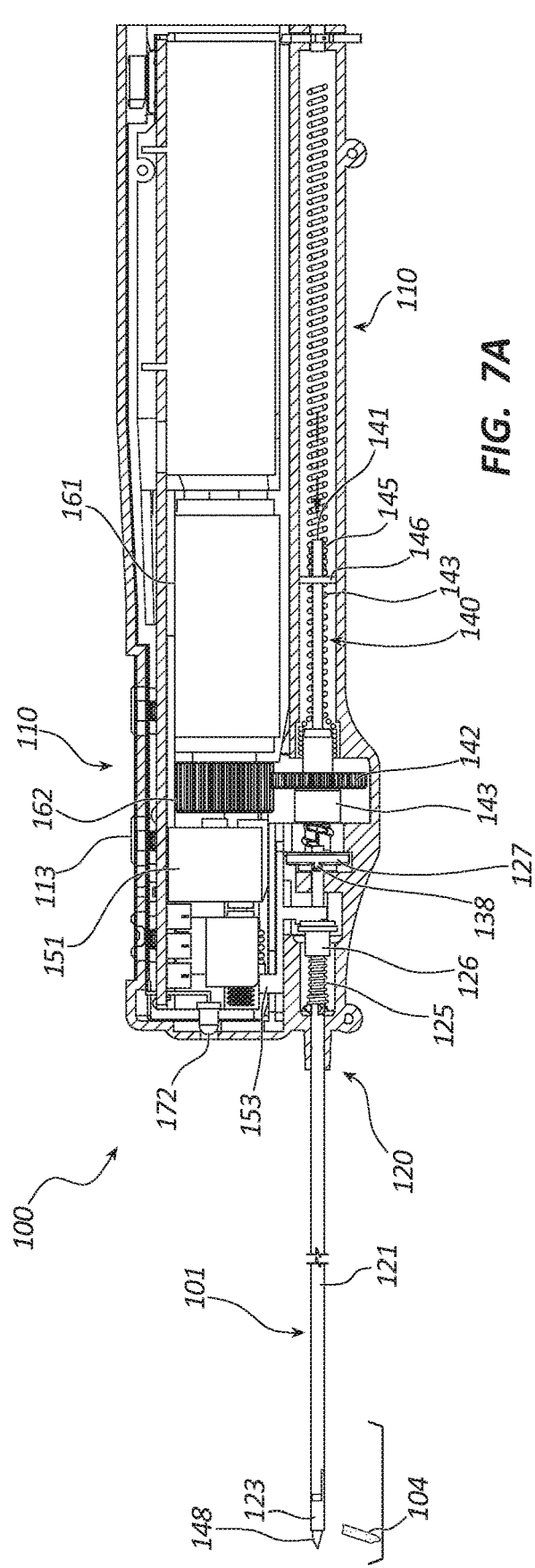
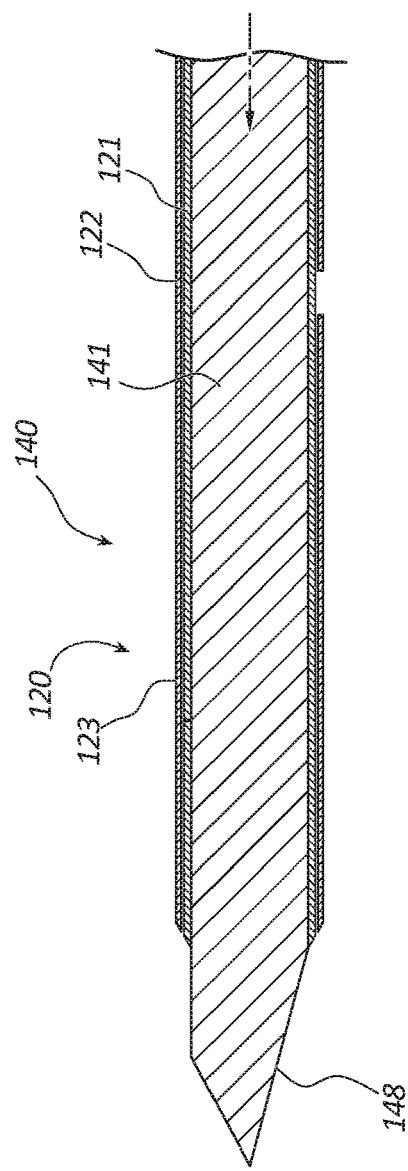
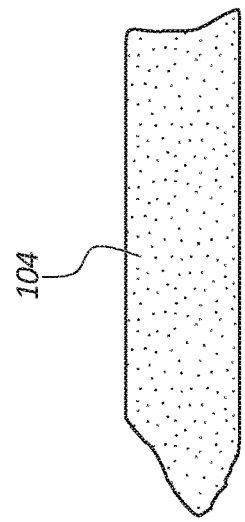
*FIG. 7A*
*FIG. 7B*

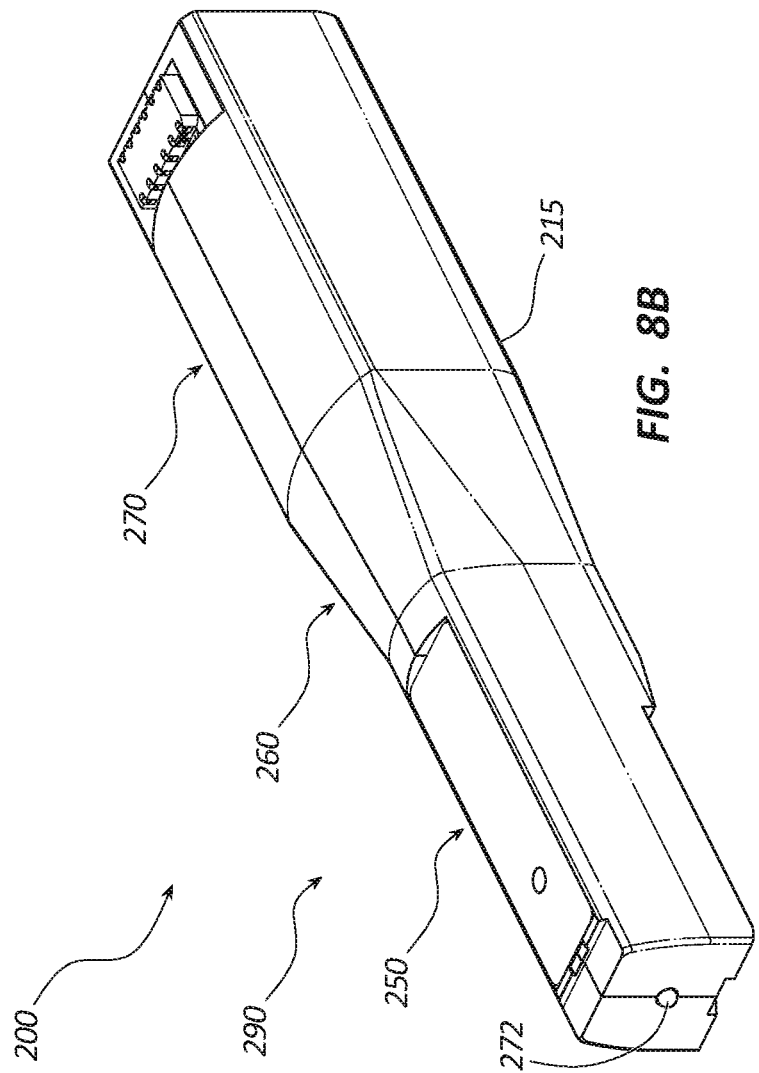

ROTATION BIOPSY SYSTEM AND HANDLE

RELATED APPLICATIONS

This application claims priority to U.S. Provisional Application No. 62/907,135, filed on Sep. 27, 2019 and titled "Rotation Biopsy System and Handle" which is hereby incorporated by reference in its entirety.

TECHNICAL FIELD

The present disclosure relates generally to devices used to acquire a tissue sample, particularly in medical devices. More specifically, the present disclosure relates to core tissue sampling tools.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 4A is a partial cross-sectional side view of the core tissue sampling tool of FIG. 1 in an insertion state.

FIG. 4B is a cross-sectional side view of a distal portion of the core tissue sampling tool of FIG. 1 in the insertion state.

FIG. 5A is a partial cross-sectional side view of the core tissue sampling tool of FIG. 1 in a tissue sampling state.

FIG. 5B is a cross-sectional side view of a distal portion of the core tissue sampling tool of FIG. 1 in the tissue sampling state.

FIG. 6A is a partial cross-sectional side view of the core tissue sampling tool of FIG. 1 in a partoff tab actuation state.

FIG. 6B is a cross-sectional side view of a distal portion of the core tissue sampling tool of FIG. 1 in the partoff tab actuation state.

FIG. 7A is a partial cross-sectional side view of the core tissue sampling tool of FIG. 1 in a tissue ejection state.

FIG. 7B is a cross-sectional side view of a distal portion of the core tissue sampling tool of FIG. 1 in the tissue ejection state.

FIG. 8B is a perspective view of a reusable member of the core tissue sampling tool of FIG. 8A.

DETAILED DESCRIPTION

Figure 1:
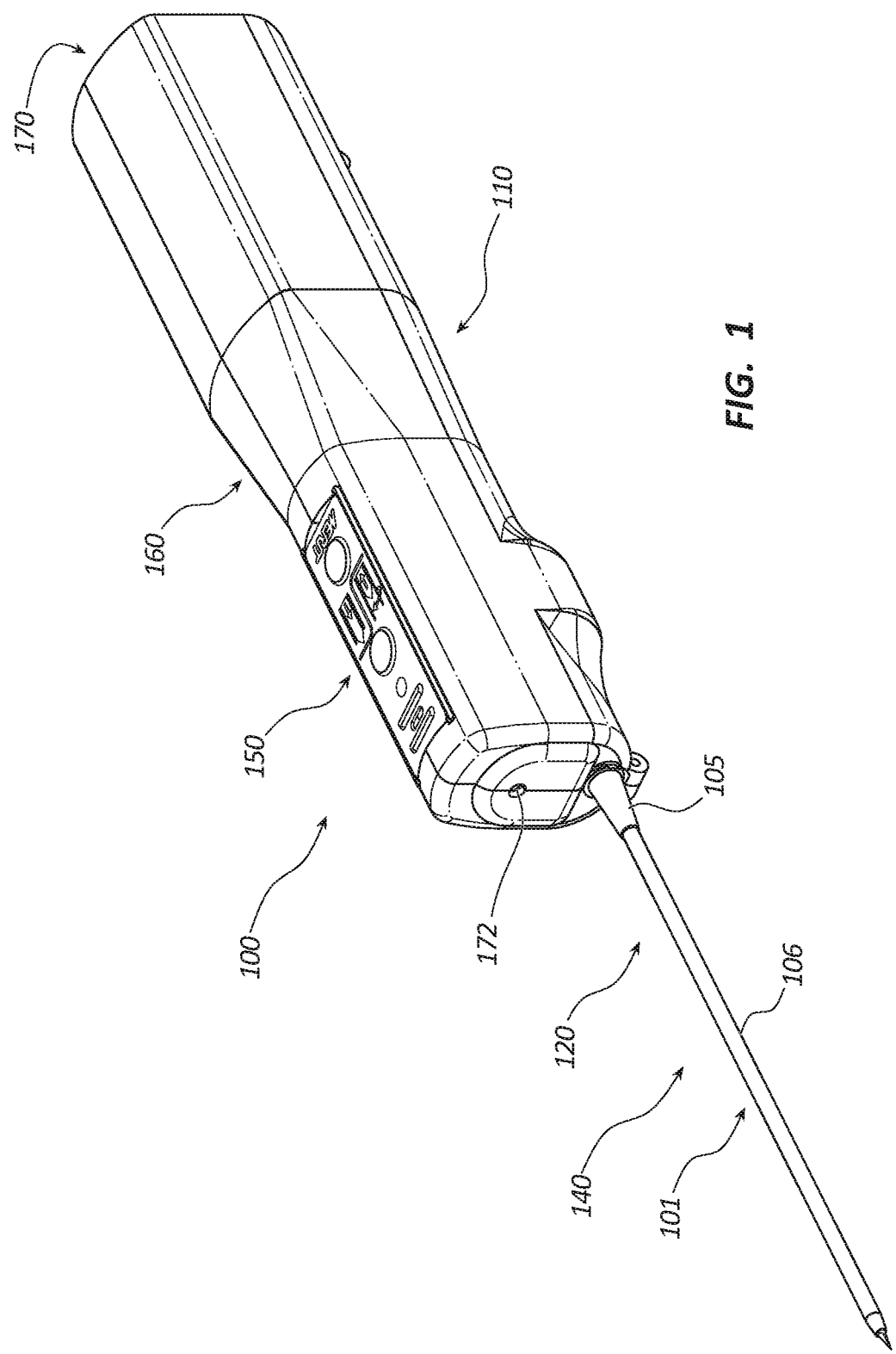
FIG. 1 is a perspective view of a core tissue sampling tool.

A core tissue sampling tool may include a handle, a trocar, a cannula assembly, a rotation drive member configured to rotate the cannula assembly and/or to longitudinally displace the trocar, and a drive member configured to actuate a partoff tab. The partoff tab may be configured to sever a portion of a tissue sample disposed within the cannula assembly from a location within a patient's body, such as from a lesion. The rotation drive member may also be configured to displace the trocar to eject the tissue sample from the cannula assembly. In some embodiments, the core tissue sampling tool may include a light source. Alternatively, or additionally, in some embodiments, the handle may include a disposable portion and a reusable portion.

The core tissue sampling tool may be used by a practitioner to acquire a core tissue sample from within the body of the patient, for example a tissue sample from a lesion with the body of the patient. In some procedures, the trocar and the cannula assemblies may be inserted into the body of the patient under ultrasound guidance to a location adjacent a target lesion. A light source may be used to illuminate the insertion site. The rotation drive member may be activated to displace the trocar proximally and to rotate the cannula assembly. As the cannula assembly is rotating it can be advanced into the lesion to sever the longitudinal portion of the tissue sample. Thus, as the cannula assembly is advanced, a tissue sample, such as a core tissue sample, may be severed along its longitudinal length and disposed within the cannula assembly. The partoff tab may be actuated while the cannula assembly is rotating, severing a distal portion of the core tissue sample from the lesion. The cannula assembly may then be withdrawn from the patient's body and the core tissue sample ejected from the cannula assembly. In other instances, the cannula assembly may be repositioned for acquisition of subsequent core tissue samples prior to withdrawal of the cannula assembly from the patient's body.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the cannula assembly portion of a core tissue sampling tool, the proximal end of the cannula assembly refers to the end nearest the handle and the distal end refers to the opposite end, the end nearest the tissue sampling end.

"Fluid" is used in its broadest sense, to refer to any fluid, including both liquids and gases as well as solutions, compounds, suspensions, etc., which generally behave as fluids. "Tissue" is also used in its broadest sense, to refer to any type of tissue, including muscle, epithelial, connective, nervous, etc., which is in the human body.

FIGS. 1-8B illustrate different views of several core tissue sampling tools and related components. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIG. 1 depicts a perspective view of an embodiment of a core tissue sampling tool 100. The sampling tool 100 may comprise a handle 110, coaxial introducer 101, cannula assembly 120, trocar assembly 140, power source 170, rotation member 160, partoff tab actuating member 150, and light source 172. The coaxial introducer 101 may include a connector 105 and a sheath 106. The coaxial introducer 101 may be disposed over distal portions of the cannula assembly 120 and trocar assembly 140. In certain embodiments, the sheath 106 may be coated with a lubricious coating, such as a hydrophilic coating, to reduce an insertion force of the sheath 106 resulting in higher quality tissue samples. The coaxial introducer 101 may be releasably coupled to the handle 110. In some embodiments, the coaxial introducer 101 may be coupled to the handle by a locking button that is configured to releasably engage with the connector 105. The locking button may include a transparent portion aligned with the light source 172 to passage of light from the light source 172 through the locking button.

Figure 2:
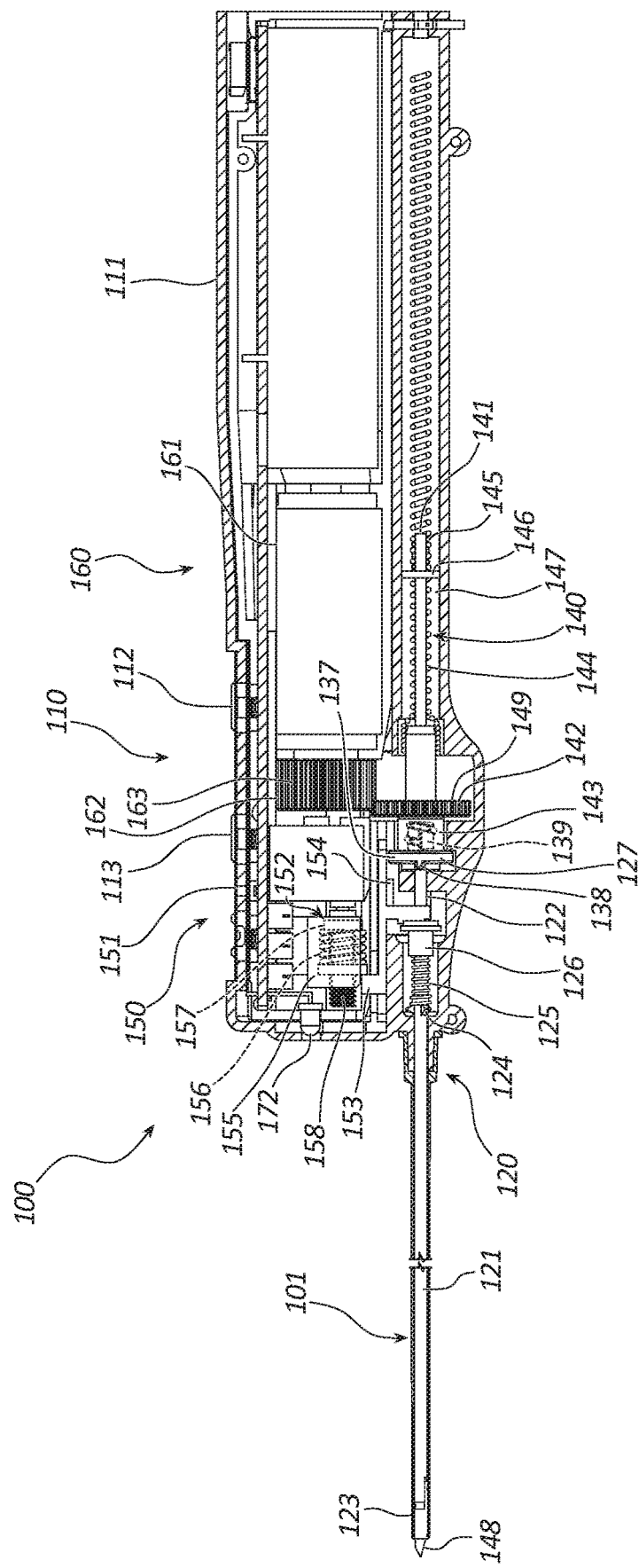
FIG. 2 is a partial cross-sectional side view of the core tissue sampling tool of FIG. 1.

FIG. 2 is a cross-sectional view of the core tissue sampling tool 100. As illustrated, the rotation member 160 includes a first motor 161 and a rotation drive member 162 fixedly coupled to the first motor 161. The first motor 161 may comprise, for example, a brushed or brushless direct current (DC) motor, a piezo motor, hydraulic or pneumatic actuator, solenoid, shape memory or muscle-wire, etc. The first motor 161 may be coupled to the power source (170 of FIG. 1) such that energy from the power source (170 of FIG. 1) may be used to cause the first motor 161 to rotate in a clockwise or counter-clockwise direction. Activation of the rotation of the first motor 161 may be caused by manipulation of a button or other actuator. In some embodiments, two or more actuators may be configured to activate the first motor 161. For example, in some embodiments, depression of either 1) a first button such as coring button 112 or 2) a second button such as ejection button 113 may be configured to activate the first motor 161. As illustrated, the rotation drive member 162 may include a circular gear having teeth 163. In other embodiments, the rotation drive member 162 may include any other suitable rotatable drive mechanism. For example, the rotation drive member 162 may include a pulley and belt, wheel, harmonic drive, hollow-shaft motor, gear box, etc.

In embodiments with a hollow-shaft motor, the cannula assembly 120 and trocar assembly 140 may be configured to slide within the hollow-shaft of the motor. In such embodiments, the rotation bushing 142 may be keyed to engage with the rotation driver member 162. Furthermore, in certain embodiments, the rotation bushing 142 may comprise magnets. In such embodiments, the magnets may be configured to engage with the rotation drive member 162. Furthermore, in embodiments wherein the motor comprises wire and magnets (such as a DC motor) the motor magnets may be coupled to rotation drive member 162 and the wire coils disposed at the location shown by motor 161 (though in such embodiments the motor may be understood as a combination of the magnets and coils).

The first motor 161 may be configured to rotate the rotation drive member 162 in both the clockwise and counter-clockwise directions. The rotation drive member 162 may be configured to operatively couple with the cannula assembly 120 and the trocar assembly 140 to facilitate their rotation in a first and a second direction relative to the clockwise and counter-clockwise rotation of the first motor. For example, in the depicted embodiment, the rotation drive member 162 is a circular gear which rotates in the same direction as the first motor 161. In another embodiment, the motor may include a gearhead configured to engage with the rotation drive member 162 and to rotate the rotation drive member 162 in a direction opposite of the first motor 161. A gear ratio of the gearhead may be about 5.3:1. Other suitable gear ratios are within the scope of this disclosure. The teeth 163 of rotation drive member 162 meshes with teeth 149 of a rotation bushing 142 of a trocar assembly 140. This results in rotation of the trocar assembly 140 in an opposite direction from the rotation direction of the first motor 161. In other words, if the first motor 161 rotates in a clockwise direction, the trocar assembly 140 will rotate in a counter-clockwise direction. In other embodiments, the first motor 161 and the trocar assembly 140 may rotate in the same direction. For convenience, rotation direction of the trocar assembly 140 and a cannula assembly 120 are described as either a first direction or a second direction with an understanding that the rotation directions may be opposite or the same as the rotation direction of the first motor 161.

The partoff tab actuating member 150 is shown in FIG. 2, and, in the illustrated embodiment, comprises a second motor 151, an actuator drive nut 152, and an actuator 153. The second motor 151 may comprise, for example, a brushed or brushless DC motor, a piezo motor, hydraulic or pneumatic actuator, solenoid, shape memory or muscle-wire, etc. The second motor 151 may be coupled to the power source (170 of FIG. 1) such that the power source (170 of FIG. 1) is configured to provide energy to cause the second motor 151 to rotate in the clockwise and the counter-clockwise directions. The actuator drive nut 152 may be coupled to the second motor 151 such that the actuator drive nut 152 is linearly displaced proximally or distally as the second motor 151 rotates.

The actuator drive nut 152 may be comprised of a carriage 155, a bushing 157 and a compliant member 156 (e.g., compression spring). The carriage 155 includes a threaded hole that engages with a leadscrew 158 coupled to the second motor 151. The carriage 155 may include flags (not shown) that are configured to engage with a limit switch (not shown). The limit switch may of any suitable type. For example, the limit switch may be a photointerrupter, magnetic reed, mechanical limit, etc. The compliant member 156 and bushing 157 may be configured to apply constant force to the actuator 153. For example, if the carriage 155 moves to a full distal position, then it might apply too much force on the actuator 153 and/or stall the second motor 151. In the illustrated embodiment, the actuator 153 contacts the bushing so that a force applied to the actuator 153 by the actuator drive nut 152 is limited by a force from the compliant member 156, causing the second motor to be less likely to stall. The actuator drive nut 152 may be selectively coupled to the actuator 153. The actuator drive nut 152 may distally displace the actuator 153 to actuate a portion of the cannula assembly 120 in an actuating state, decouple from the actuator 153 in a neutral state, and proximally displace the actuator 153 in an anti-rotation state. The actuator 153 may further comprise an anti-rotation feature 154 distending, for example, from a proximal portion. The anti-rotation feature 154 may be configured to engage with a portion of the cannula assembly 120 to prevent rotation of the cannula assembly 120 in the second direction. In another embodiment, the partoff tab actuating member 150 may not comprise the second motor 151. In this embodiment the partoff tab actuating member may include a spring-loaded mechanism activated by a depressible button.

As depicted in FIG. 2, the cannula assembly 120 may include an outer cannula 121, an inner cannula 122, a partoff tab 123, a limiting tab 124, a resilient member 125, an actuation bushing 126, and a decoupling bushing 127. The inner cannula 122 is shown to be coaxially disposed within the outer cannula 121. Distal portions of the cannulas 121, 122 extend from the handle 110 while proximal portions are disposed within the handle 110. A collective distal end of the cannulas 121, 122 may be circumferentially sharpened to provide a circular cutting edge. In other embodiments, the collective distal ends of the cannulas may be sharpened by swaging, lubrication, drawing, etc. The cannulas 121, 122 may be formed of a variety of materials, including, for example, stainless steel, nitinol, titanium, etc. In some embodiments, the inner cannula 122 may include a helical protrusion extending into a lumen. The helical protrusion may be configured to facilitate tissue sampling when the inner cannula is rotated. In certain embodiments, the outer cannula 121 may be coated with a lubricious coating, such as a hydrophilic coating, to reduce an insertion force of the outer cannula 121 resulting in higher quality tissue samples.

Figure 3C:
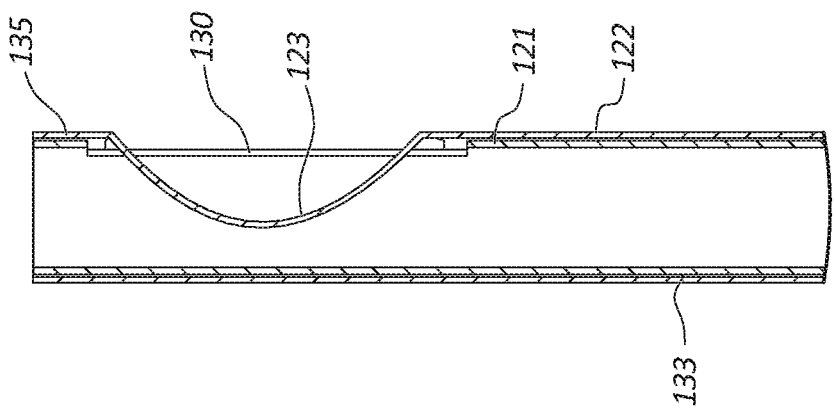
FIG. 3C is a cross-sectional side view of a distal portion of the cannula assembly of the core tissue sampling tool of FIG. 1 with a partoff tab in an actuated state.
Figure 3B:
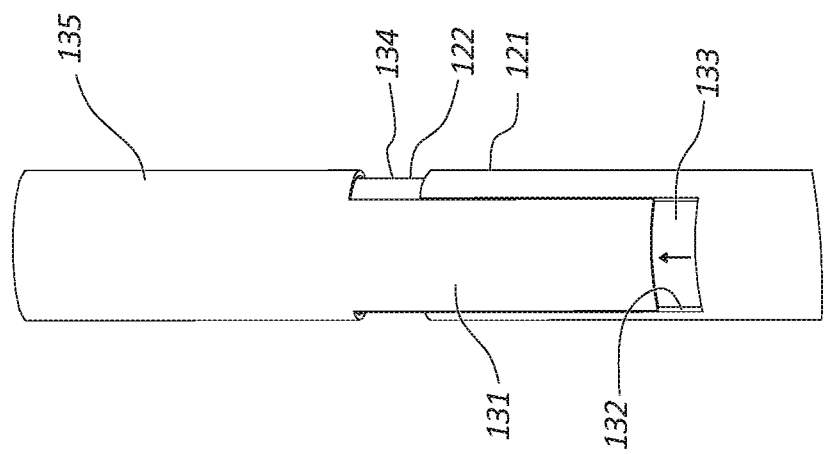
FIG. 3B is a bottom view of a distal portion of the cannula assembly of the core tissue sampling tool of FIG. 1.
Figure 3A:
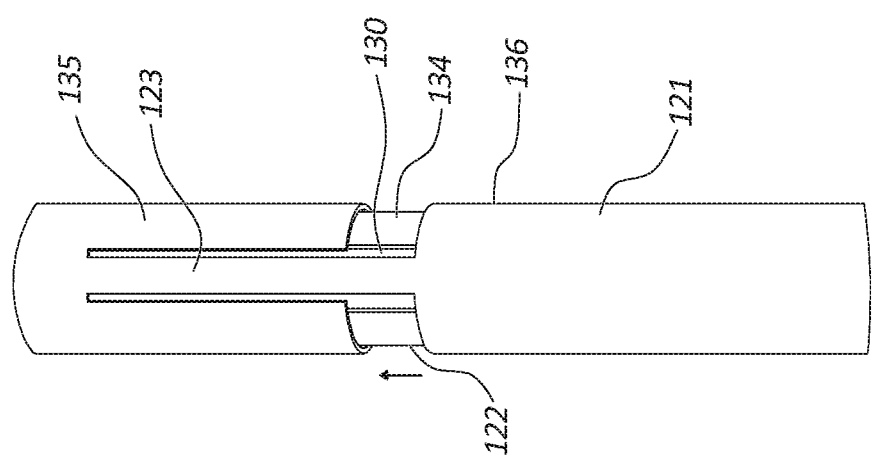
FIG. 3A is a top view of a distal portion of a cannula assembly of the core tissue sampling tool of FIG. 1.

FIGS. 3A-3B depict a distal portion of the cannula assembly 120 with the partoff tab 123 in a non-actuated state; FIG. 3A is a top view of the distal portion of the cannula assembly 120 and FIG. 3B is a bottom view of the distal portion of the cannula assembly. As shown in FIGS. 3A-3B, the partoff tab 123 is disposed adjacent a distal end of the cannula assembly 120. In the illustrated embodiment, the partoff tab 123 is coupled to a middle portion 136 and a distal portion 135 of the outer cannula 121 and disposed over an aperture 130 of the inner cannula 122. As shown in the embodiment of the figures, the outer cannula 121 is also fixedly coupled to the inner cannula 122 at a location distal to the partoff tab 123. These elements may be coupled in a variety of ways, for example, the outer cannula 121 and the inner cannula 122 may be coupled by welding, gluing, swaging, etc. Additionally, in the illustrated embodiment, a tab 131 of the distal portion 135 disposed opposite of the partoff tab 123 and extends proximally into a tab receiver 132 of the middle portion 136. A tab gap 133 is defined by the tab 131 and the tab receiver 132. A gap 134 is defined between the distal portion 135 and the middle portion 136 when the partoff tab 123 is in the non-actuated state, as shown in FIGS. 3A-3B.

FIG. 3C is a cross-sectional side view the partoff tab 123, shown in an actuated state (as compared to the non-actuated state of FIGS. 3A-3B). As shown in the figures, in the illustrated embodiment, the actuated state may be achieved when the outer cannula 121 is distally displaced relative to the inner cannula 122. This distal displacement may be caused by distal displacement of the actuator 153 by the actuator drive nut 152. The distal displacement of the outer cannula 121 can close the tab gap 133 and the gap 134. In another embodiment, a length of the gap 134 may be longer than a length of the tab gap 133. In this embodiment, the tab cap 133 may be closed while the gap 134 remains open to prevent capture of tissue in the gap 134. Closing of the gaps 133, 134 may displace a proximal end of the partoff tab 123 towards a distal end and effectively shortens the longitudinal length along an axis of the cannula assembly 120 between proximal and distal ends of the partoff tab 123. The partoff tab 123 may be configured to be deflected radially inward through the aperture 130 into the lumen of the inner cannula 122 when the gaps 133, 134 are closed or otherwise moved together. In some embodiments, the partoff tab 123 may be pre-biased inwardly in the non-actuated state to facilitate inward radial deflection. The partoff tab 123 may be deflected from about 50% to about 90%, from about 60% to about 80%, or from about 70% to about 80% of an internal diameter of the inner cannula 122. The partoff tab 123 (in the actuated state) can be configured to sever a distal portion of a tissue sample disposed within the inner cannula 122 from the body and to retain the tissue sample within the inner cannula 122 when the cannula assembly 120 is withdrawn from a patient's body. In some embodiments, the partoff tab 123 may be annealed or treated otherwise to increase the strength of the partoff tab 123 such that the partoff tab 123 may withstand multiple actuations.

Referring again to FIG. 2, a proximal end of the outer cannula 121 may be fixedly coupled to an actuation bushing 126, for example, by gluing, welding, overmolding, stamping, laser cutting, etc. The outer cannula 121 may include a limiting tab 124 disposed distally of the actuation bushing 126. In some embodiments, the limiting tab 124 may be formed by cutting the wall of the outer cannula 121 to define at least one longitudinal limiting tab 124 and deforming the cut portion such that the limiting tab 124 extends radially outward from the outer cannula 121 wall. For example, the outer cannula 121 may be longitudinally compressed relative to the inner cannula 122 such that the limiting tab 124 is deflected radially outward. The limiting tab 121 may be welded to the inner cannula 122 such that the inner cannula 122 and the outer cannula rotationally locked together. A resilient member 125 (such as, for example, a spring) may be disposed between the actuation bushing 126 and the limiting tab 124. In the illustrated embodiment, when the partoff tab 123 is actuated, the actuator 153 engages with the actuation bushing 126 and displaces the actuation bushing 126 and a portion of the outer cannula 121 distally relative to the inner cannula 122 such that the gaps 133, 134 are at least partially closed and the resilient member 125 is compressed between the limiting tab 124 and the actuation bushing 126. When the partoff tab 123 is returned to the non-actuated state, the actuator 153 disengages from the actuation bushing 126 and the resilient member 125 displaces the actuation bushing 126 and the portion of the outer cannula 121 proximally, opening the gaps 133, 134 and returning the partoff tab 123 to the non-actuated state.

As illustrated in FIG. 2, a proximal end of the inner cannula 122 is fixedly coupled to a decoupling bushing 127. The decoupling bushing 127 may include a circular flange 137 having a nub 138 extending distally from a distal face of the flange 137. The nub 138 can engage with the anti-rotation feature 154 of the actuator 153 to restrict rotation of the decoupling bushing 127 in the second direction when the actuator 153 is displaced proximally. In other words, the decoupling bushing 127 may be free to rotate in both the first and second directions until the actuator 153 is displaced proximally, such as when a core tissue sample is ejected from the sample tool, as will be explained below. In another embodiment, the core tissue sampling tool 100 may include a split washer ratchet that allows the decoupling busing to rotate in only one direction. An external threaded portion 139 may extend proximally from the flange 137. The threaded portion 139 may be configured to threadingly couple to, and decouple from, a rotation bushing 142 of the trocar assembly 140. When coupled, the rotation bushing 142 may be coupled to the rotation drive member 162 such that the rotation bushing 142, the cannula assembly 120, and a portion of the trocar assembly 140 can be rotated in the first direction. Rotation of the rotation bushing 142 in the second direction by the rotation drive member 162 decouples the decoupling bushing 127 from the rotation bushing 142 because the decoupling bushing 127 is prevented from rotating in the second direction by the anti-rotation feature 154. In another embodiment, when the actuator is in a distal position, the rotation drive member 162 may be rotated in the second direction by the first motor 161 to decouple the rotation drive member 162 from the bushing 127. When decoupled, the decoupling bushing 127 and the cannula assembly 120 are not rotated in the second direction while the portion of the trocar assembly 140 is rotated in the second direction.

In some embodiments, the trocar assembly 140 may include the trocar 141, the rotation bushing 142, an externally threaded member 144, and a nut 145. As depicted in FIG. 2, the rotation bushing 142 may be configured as a circular gear having a plurality of teeth 149. The teeth 149 may be configured to mesh with the teeth 163 of the rotation drive member 162. In other embodiments, the rotation bushing 142 may be configured as a bearing, a pulley wheel, etc., or any other rotation driving mechanism. The rotation bushing 142 may include an internally threaded portion 143 configured to threadingly couple with and decouple from the decoupling bushing 127 as described above. In other embodiments, the internally threaded portion 143 may extend from the externally threaded member 144.

As shown in FIG. 2, in the illustrated embodiment, the trocar 141 is coaxially disposed within the inner cannula 122. The trocar 141 is configured to be proximally and distally translated within the inner cannula 122. The trocar 141 may be a rod formed from a variety of materials, including rigid materials, for example, including, stainless steel, titanium, nitinol, rigid plastics, etc. In some embodiments, the trocar 141 may be a tube having a lumen. The trocar 141 can comprise a sharp distal end 148 configured to penetrate tissue. The distal end 148 may include a plurality of facets and a sharp point. In other embodiments, the distal end 148 may include a bevel, a pencil point, or other tissue penetrating geometries or configurations. In other embodiments, the trocar 141 may be blunt. In another embodiment, the sharp trocar 141 may be replaced with a blunt trocar prior to ejection of a tissue sample from the cannula assembly 120.

The externally threaded member 144 may be fixedly coupled to and extend proximally from the rotation bushing 142 to adjacent a proximal end of the housing 111. For example, a distal portion of the threaded member 144 can be disposed over a proximal portion of the rotation bushing 142 as depicted in FIG. 2. In another embodiment, the distal portion of the threaded member 144 may be disposed within the proximal portion of the rotation bushing 142. Embodiments wherein the threaded member 144 is press fit into the rotation bushing 142 are within the scope of this disclosure. The threaded member 144 may be disposed around a portion of the trocar 141. As shown in FIG. 2, the threaded member 144 may comprises an elongate coil configured to longitudinally translate the nut 145 when rotated. In some embodiments, the nut 145 may be longitudinally translated by pulse wave modulation, magnetic force, compressed gas, etc. The threaded member 144 may be formed of a wire or rod made of a rigid material. For example, the wire or rod may be formed from stainless steel, titanium, polymers such as polycarbonate, etc. The pitch of the coils may be determined by the number of rotations of the threaded member 144 desired to translate the nut 145 from a proximal end to a distal end of the threaded member 144. The coil pitch may range from about 0.01 inch to about 0.20 inch, from about 0.04 inch to about 0.15 inch, or from about 0.06 inch to about 0.10 inch. In other embodiments, the threaded member 144 may be an externally threaded tube, a threaded rail, external threading on the trocar, etc.

The nut 145 may be configured to be threadingly coupled with the threaded member 144 such that when the threaded member 144 is rotated in the first direction the nut 145 is translated proximally and when the threaded member 144 is rotated in the second direction the nut 145 is translated distally. The geometry of the nut 145 and threaded member 144 may be matched to reducing or eliminate binding, including geometry to facilitate engagement between the nut 145 and end of the threaded member 144 without binding. As illustrated in FIG. 2, the nut 145 is configured as a coiled nut. The coiled nut may be formed of a wire or rod made of a rigid material. For example, the wire or rod can be formed from stainless steel, titanium, polymers such as polycarbonate, etc. The diameter of the wire or rod of the coiled nut may be sized to slidingly fit between the coils of the threaded member 144. The coiled nut 145 may include at least one radially outward extending arm 146 configured to slidingly couple within a longitudinal channel 147 within the housing 111. The channel 147 is configured to guide and prevent rotation of the nut 145 relative to the threaded member 144 such that orientation of the distal end 148 of the trocar 141 may be maintained. The channel 147 and nut 145 may center the trocar 141 both horizontally and vertically relative to the cannula assembly 120. In another embodiment, the nut 145 may include a larger end diameter than a body diameter to facilitate threading of the nut 145 onto the threaded member 144. In other embodiments, the nut 145 may be an internally or externally threaded nut.

The nut 145 may be fixedly coupled (e.g., welded) to a proximal portion of the trocar 141, such that when the nut 145 is longitudinally translated, the trocar is longitudinally translated relative to the cannula assembly 120. In other words, when the rotation bushing 142 is rotated in the first direction by the rotation drive member 162, the threaded member 144 is also rotated in the first direction and the nut 145 and trocar 141 are translated proximally. When the rotation bushing 142 and threaded member 144 are rotated in the second direction, the nut 145 and trocar 141 are translated distally. The nut 145 may decouple from the threaded member 144 adjacent the proximal end of the threaded member 144 as the threaded member 144 is rotated in the first direction. When decoupled, continued rotation of the threaded member 144 will not result in further proximal translation of the nut 145 and trocar 141. When the threaded member 144 is rotated in the second direction, a distal end of the threaded member 144 couples to the arm 146 of the nut 145 resulting in distal translation of the nut 145 and the trocar 141. To facilitate coupling of the threaded member 144 with the nut 145 when the threaded member 144 is rotated in the second direction, the rotation bushing 142 may be displaced proximally when rotationally decoupling from the decoupling bushing 127 such that a proximal end of the threaded member 144 can couple with the nut 145. For example, the threaded member 144 may be displaced proximally such that an end coil of the coiled thread engages with the arm 146 to initiate coupling of the coils of the coiled nut with the coils of the coiled thread.

In some embodiments, a trocar may include an arm coupled to a proximal end and extending outside of a handle. The arm may be manually longitudinally displaced by a clinician to translate the trocar proximally and distally. The arm may also lock the trocar in a distal or proximal position. In other embodiments, the trocar may be manually displaced distally and displaced proximally by a resilient member. In another embodiment, a trocar may include grooves or notches cut into an exterior surface. The grooves or notches may couple with a pinion to displace the trocar longitudinally. In yet another embodiment, a trocar may be longitudinally displaced using electronic or magnetic members. For example, the trocar may be displaced by an electromagnet, a permanent magnet, a member formed from a shape memory alloy, such as nitinol, a muscle wire, or a variety of other electronic or magnetic elements. In yet another embodiment, a trocar may be longitudinally displaced by a pneumatic or hydraulic force. In another embodiment, a trocar may be formed from a flexible material to allow the trocar to bend and compress to a shorter length in order to shorten a length of a handle.

As shown in FIG. 2, a light source 172 may be disposed at a distal end of the handle 110. The light source 172 may include one, two, three, or more light emitting diodes (LED) and/or other light generating elements. For example, the light source 172 may be incandescent bulbs, halogen bulbs, krypton bulbs, etc. In some instances, plurality of LEDs, disposed at various positions, may be used to eliminate shadows when illuminating the work site. The light source 172 may be a single color or a multicolor LED. A multicolored LED may be configured to indicate different functions of the tissue sampling tool 100, such as, for example, activation of rotation of the cannula assembly 120, initiation of tissue sample ejection, status of a battery's charge, etc. Additionally, or alternatively, the light source 172 may be configured to flash in order to indicate a state or function of the sampling tool 100, such as to indicate the device is ejecting a sample. An angle of illumination from the light source 172 may range from about 5 degrees to about 150 degrees, from about 10 degrees to about 45 degrees, and from about 15 degrees to about 30 degrees to focus the illumination within a narrow field. The intensity of the light source 172 may vary during a core tissue sampling procedure to indicate different phases of the procedure and functions of the sampling tool 100. The light source 172 may be independently actuated, or may be actuated in connection with other functions of the sampling tool 100. For example, the light source 172 may be controlled by the coring button 112 and/or the ejection button 113 of the handle 110. For example, the light source 172 may be activated when the coring button 112 is depressed to illuminate the work site and deactivated when the coring button 112 is released, thus illuminating the worksite while the coring function is in operation. The light source 172 may also be activated when the ejection button 113 is depressed to illuminate the tissue samples. Again, in other embodiments, the light source 172 may be independently controlled, such as by a dedicated button. The intensity of the light source 172 may be controlled by the amount of depression of the dedicated button or through other controls. The light source 172 may be configured to illuminate a work area, such as a tissue sampling site, to help locate and orient the sampling tool 100 when in a darkened room, to illuminate acquired tissue samples when ejected from the sampling tool 100, and to indicate a status of the sampling tool 100, etc.

FIGS. 4A-7B depict an exemplary series of configurations illustrating the tissue sampling tool 100 in use for a particular therapy. More particularly, FIG. 4A depicts the tissue sampling tool 100 in an insertion state and FIG. 4B depicts distal portions of the cannula assembly 120 and the trocar assembly 140 in the insertion state. FIG. 5A depicts the tissue sampling tool 100 in a tissue coring or sampling state and FIG. 5B depicts distal portions of the cannula assembly 120 and the trocar assembly 140 in the tissue coring or sampling state. FIG. 6A depicts the tissue sampling tool 100 in a sample partoff state and FIG. 6B depicts distal portions of the cannula assembly 120 and the trocar assembly 140 in the sample partoff state. FIG. 7A depicts the tissue sampling tool 100 in a tissue sample ejection state and FIG. 7B depicts distal portions of the cannula assembly 120 and the trocar assembly 140 in the tissue sample ejection state.

Referring to FIG. 4A, the tissue sampling tool 100 is depicted with the distal portions of the cannula assembly 120, trocar assembly 140 and introducer 101 inserted into, and disposed within, a patient's body. In some embodiments, the introducer 101 is not used to insert the tissue sampling tool 100 into the patient's body. The insertion of the tissue sampling tool 100 may be accomplished using any suitable guidance technique. For example, the insertion may be accomplished under ultrasound imaging guidance, under fluoroscopy imaging guidance, using palpation, etc. FIG. 4A further illustrates the handle 110 in the insertion state where the rotation drive member 162 is coupled with the rotation bushing 142, the rotation bushing 142 is positioned distally within a recess of the housing 111 and coupled to the decoupling bushing 127, the actuator 153 is in the neutral state, and the actuation bushing 126 is positioned proximally. The light source 172 may be activated to illuminate the working field or insertion site.

FIG. 4B shows the distal end 148 of the trocar 141 extending from inner and outer cannulas 122, 121 and disposed adjacent to the lesion 103, the partoff tab 123 in the non-actuated state where the partoff tab 123 does not extend into the lumen of the inner cannula 122 and the coaxial introducer is disposed over the inner and outer cannulas 122, 121.

Referring to FIG. 5A, the tissue sampling tool 100 is depicted with the distal portions of the cannula assembly 120, trocar assembly 140 and introducer 101 inserted into and disposed within a lesion 103 when obtaining a core tissue sample as the inner and outer cannulas 122, 121 are rotated. FIG. 5A further illustrates the handle 110 in the tissue coring state where rotation of the first motor 161 is activated when the clinician depresses the first or coring button 112. The first motor 161 may be configured to ramp up to speed over a short period of time (e.g., 0.25 second) to prevent torqueing or jerking of the tissue sampling tool 100. During tissue coring, a rotational speed of the first motor 161 may be up to 100% of a maximum rotational speed of the first motor 161. The rotational speed and power to the first motor 161 may be controlled by pulse width modulation. The first motor 161 rotates the rotation drive member 162 which rotates the rotation bushing 142 in a first direction. The rotation bushing 142 rotates the decoupling bushing 127 in the first direction. The decoupling bushing 127 rotates the inner cannula 122 in the first direction. The inner cannula 122 rotates the outer cannula 121 in the first direction. The rotational bushing 142 also rotates the threaded member 144 in the first direction. The nut 145 and the trocar 141 are translated proximally until the nut 145 decouples from the threaded member 144 adjacent the proximal end of the threaded member 144. The distal end 148 of the trocar 141 is disposed within the inner cannula 122. The distal end 148 may be disposed at least 6 cm from the distal end of the outer cannula 121 to accommodate multiple tissue samples. The actuator 153 is in the neutral state, and the actuation bushing 126 is positioned proximally. The light source 172 may be activated to illuminate the working field or insertion site.

FIG. 5B shows the distal end 148 of the trocar 141 disposed within the inner cannula 122. The circumferentially sharpened distal ends of the inner and outer cannulas 122, 121 and the coaxial introducer 101 are advanced into the lesion as they are rotated, severing a longitudinal portion of the tissue sample. A core tissue sample 104 is procured within the lumen of the inner cannula 122. The partoff tab 123 is in the non-actuated state where the partoff tab 123 does not extend into the lumen of the inner cannula 122.

Referring to FIG. 6A, the tissue sampling tool 100 is depicted with the distal portions of the cannula assembly 120, trocar assembly 140 and introducer 101 disposed within a lesion 103 at the conclusion of severing of the core tissue sample 104. FIG. 6A further illustrates the handle 110 in the tissue partoff state where the first motor 161 continues to rotate and the partoff tab actuation motor or second motor 151 is activated when the clinician releases digital pressure from the first or coring button 112. The second motor 151 may be configured to ramp up to speed over a short period of time (e.g., 0.25 second) to prevent torqueing or jerking of the tissue sampling tool 100. The first motor 161 continues to rotate resulting in a rotation of the cannula assembly 120 and the trocar assembly 140 in the first direction. The second motor 151 distally translates the actuator drive nut 152. The actuator drive nut 152 engages with the actuator 153 and displaces it distally. The actuator 153 engages with the actuation bushing 126 and displaces it distally. The actuation bushing 126 applies a compressive force to the resilient member 125 and displaces the middle portion 136 of the outer cannula 121 distally, as indicated by the arrow. The middle portion 136 applies a longitudinal force to the partoff tab 123 causing the partoff tab 123 to radially deflect through the aperture 130 into the lumen of the inner cannula 122 while the inner and outer cannulas 122, 121 are rotating as illustrated in FIG. 6B. The deflected partoff tab 123 may sever a distal portion of the core tissue sample 104, separating the sample from the lesion 103. The second motor 151 may be activated until a threshold load is applied by the actuator 153. In another embodiment, the second motor 151 may be activated for a specified period of time. In yet another embodiment, the partoff tab actuation motor 151 may be activated until a threshold voltage is drawn by the second motor 151 to indicate actuation of the partoff tab 123. In still another embodiment, the second motor 151 may be activated until the actuator drive nut 152 triggers a limit switch. Following actuation of the partoff tab 123 and severing of the core tissue sample 104, the first motor 161 and the second motor 151 are deactivated and rotation is stopped. The first motor 161 may continue to rotate for a period of time (e.g., 0.25 second, 0.5 second, or 1.0 second) after the second motor 151 has stopped. The light source 172 may also be deactivated. In certain embodiments, procurement of additional tissue samples may be achieved without removal of the tissue sampling tool 100. The tissue sampling tool 100 may be redirected to a different location within the lesion 103 and the processes of coring and tissue sample severing may be repeated.

FIG. 6B shows the distal end 148 of the trocar 141 disposed within and proximal to a distal end of the inner cannula 122. The distal end 148 may be disposed proximally at least 6 cm form the distal end of the inner cannula to accommodate one, two, three, four, or more tissue samples 104. As described above, during the initial portion of this step the distal portions of the inner and outer cannulas 122, 121 continue to rotate within the coaxial introducer 101. A core tissue sample 104 is disposed within the lumen of the inner cannula 122. The partoff tab 123 is shown actuated where the partoff tab 123 extends into the lumen of the inner cannula 122. The partoff tab 123 rotates with the inner and outer cannulas 122, 121 relative to the lesion 103 and severs a distal portion of the core tissue sample 104 from the lesion 103.

Referring to FIG. 7A, the tissue sampling tool 100 is depicted with the distal portions of the cannula assembly 120 and trocar assembly 140 removed from the introducer 101 and patient's body in preparation for ejection of the core tissue sample 104 from the tissue sampling tool 100. FIG. 7A further illustrates the handle 110 in the tissue ejection state where the second or ejection button 113 is depressed by the clinician to activate the second motor 151 to translate the actuator drive nut 152 proximally. The actuator drive nut 152 displaces the actuator 153 proximally from the actuation state to the anti-rotation state. The actuation bushing 126 is displaced proximally by a decompressive force applied by the resilient member 125. The actuation bushing 126 displaces the outer cannula 121 proximally and the partoff tab returns to the undeflected state. The anti-rotation feature 154 of the actuator 153 engages with the nub 138 of the decoupling bushing 127 to prevent rotation of the decoupling bushing 127 and the cannula assembly 120 in the second direction. The rotation bushing 142 is rotated by the first motor 161 in the second direction where it rotationally decouples from the decoupling bushing 127 and translates proximally. The rotation bushing 142 rotates the threaded member 144 in the second direction. A rotational speed of the first motor 161 during tissue sample ejection may be about 30% to about 70%, from about 40% to about 60%, and about 50% of the maximum rotation speed of the first motor 161. The distal end of the threaded member 143 couples with the nut 145 resulting in a distally directed translation of the nut 145 and the trocar 141 to eject the tissue sample 104 from the inner cannula 122. The light source 172 may flash as an indicator of an initiation of ejection of the tissue sample 104.

FIG. 7B shows the distal portions of the cannula assembly 120 and trocar assembly 140 removed from the patient's body. In some embodiments, the introducer 101 (not shown) may remain inserted into the patient's body to facilitate procurement of additional tissue samples. In certain embodiments, the deflected partoff tab 123, as illustrated in FIG. 6B, may prevent a vacuum force from pulling the tissue sample 104 from the inner cannula 122 when the tissue sampling tool 100 is removed from the patient's body. As depicted in FIG. 7B, the partoff tab 123 is in the undeflected state. The distal end 148 of the trocar 141 is displaced distally to displace the tissue sample 104 from the inner cannula 122. The distal end 148 of the trocar 141 extends from the distal end of the inner and outer cannulas 122, 121. The tissue sample 104 is shown ejected from the cannulas 122, 121. In some embodiments, the tissue sample 104 may be collected on a specimen collection plate or tray. In other embodiments, the tissue sample may be ejected into a tissue preserving fluid, such as formalin, contained within a specimen collection jar.

Figure 8A:
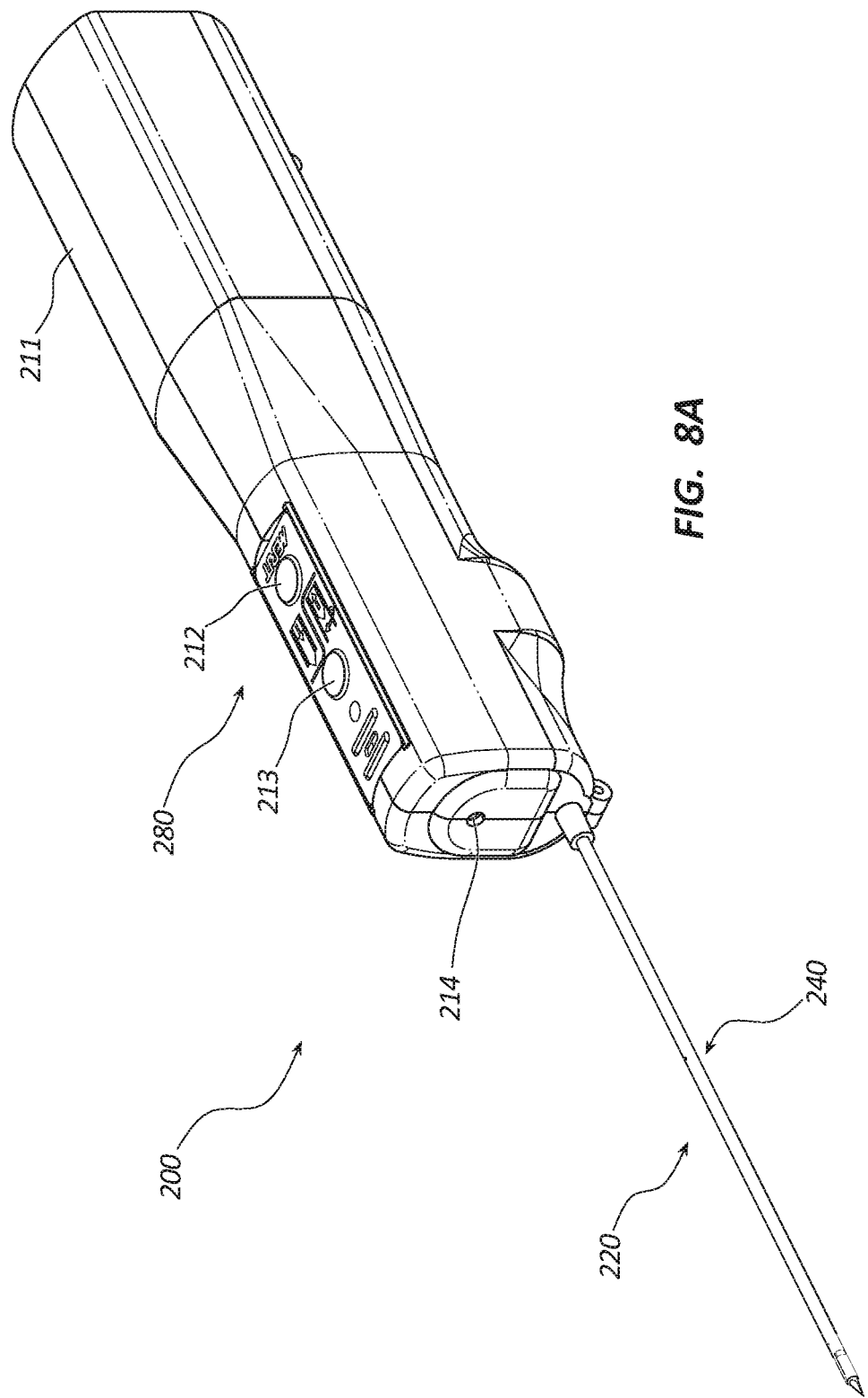
FIG. 8A is a perspective view of a disposable member of another core tissue sampling tool.

FIGS. 8A-8B depict an embodiment of a tissue sampling tool 200 that resembles the tissue sampling tool 100 described above in certain respects. Accordingly, like features are designated with like reference numerals, with the leading digit incremented to "2." For example, the embodiment depicted in FIGS. 8A-8B includes a handle 210 that may, in some respects, resemble the handle 110 of FIG. 1. Relevant disclosure set forth above regarding similarly identified features thus may not be repeated hereafter. Moreover, specific features of the tissue sampling tool 100 and related components shown in FIGS. 1-7B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the tissue sampling tool 200 and related components depicted in FIGS. 8A-8B. Any suitable combination of the features, and variations of the same, described with respect to the tissue sampling tool 100 and related components illustrated in FIGS. 1-7B can be employed with the tissue sampling tool 200 and related components of FIGS. 8A-8B, and vice versa.

The tissue sampling tool 200 of FIGS. 8A-8B can include a disposable member 280 as illustrated in FIG. 8A and a reusable member 290 as illustrated in FIG. 8B. The disposable member 280 may include an outer housing 211, a cannula assembly 220, a trocar assembly 240, a coring activation button 212, and an ejection activation button 213 as previously describe relative to tissue sampling tool 100. A cavity within the outer housing 211 is configured to receive the reusable member 290. The outer housing 211 may include a latch disposed at a proximal end of the cavity to retain the reusable member 290 within the cavity. In other embodiments, the outer housing 211 may include an openable and closeable cavity closure or door hingedly coupled to the proximal end of the outer housing 211. In another embodiment, the door may be configured to translate vertically and pivot axially when opened and closed. The disposable member 280 may be configured to be handled by a user and exposed to contaminants, such as bodily fluids, while protecting the reusable member 290 from contamination. The disposable member 280 may be sterilized and presented for use in a sterilized package.

The reusable member 290 may include an inner housing 215, a power source 270, a rotation member 260, a partoff tab actuating member 250, and a light source 272 as previously described relative to the tissue sampling tool 100. As shown in FIG. 8B, the reusable member 290 may be configured to be disposed within the cavity of the disposable member 280 such that the light source 272 is disposed adjacent a distal end of the outer housing 211. When disposed within the outer housing 211, a light port 214 is aligned with the light source 272 and the rotation member 260 is coupled to the trocar assembly 240.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A tool for acquiring a tissue sample, comprising:
   a handle;
   a cannula assembly, the cannula assembly comprising:
   an outer cannula;
   an inner cannula coaxially disposed within the outer cannula, wherein a portion of the outer cannula is axially slidable relative to the inner cannula;
   a partoff tab coupled to the outer cannula;
   a trocar assembly;
   a rotation member configured to rotate the cannula assembly in a first direction and the trocar assembly in the first direction and a second direction;
   an anti-rotation feature configured to engage with a portion of the cannula assembly to prevent rotation of the cannula assembly in the second direction while permitting rotation in the first direction;
   a decoupling bushing comprising a circular flange having a nub extending distally from a distal face of the flange; and
   a partoff tab actuation member,
   wherein the inner cannula is fixedly coupled to the decoupling bushing, and wherein the nub engages with the anti-rotation feature to restrict rotation of the decoupling bushing and the cannula assembly in the second direction while permitting the rotation in the first direction when the anti-rotation feature is displaced proximally as the tissue sample is ejected from the tool.

2. The tool of claim 1, wherein the outer and inner cannulas are configured to rotate together in the first direction.

3. The tool of claim 1, wherein the inner cannula comprises a helical projection disposed on an internal surface and extending into a lumen configured to longitudinally displace the tissue sample when the inner cannula is rotating.

4. The tool of claim 1, wherein the partoff tab is configured to retain the tissue sample within the inner cannula when the partoff tab is in an actuated state.

5. The tool of claim 1, wherein the partoff tab is configured to sever the tissue sample from a lesion when in an actuated state and the cannula assembly is rotated.

6. The tool of claim 1, wherein the trocar assembly comprises:
a trocar comprising a sharp distal end and slidingly disposed within the cannula assembly;
an externally threaded member; and
an internally threaded nut fixedly coupled to the trocar and operatively coupled to the externally threaded member.

7. The tool of claim 6, wherein the internally threaded nut is configured to proximally displace the trocar when the externally threaded member is rotated in the first direction and to distally displace the trocar when the externally threaded portion member is rotated in the second direction.

8. The tool of claim 1, wherein the rotation member comprises:
a first motor;
a first rotation drive member coupled to the first motor, the cannula assembly, and the trocar assembly; and
a power source.

9. The tool of claim 1, wherein the partoff tab actuation member comprises:
a second motor;
a partoff tab actuator coupled to the second motor, wherein the partoff tab actuator comprises a neutral state, a partoff tab actuation state, and an anti-rotation state; and
a power source.

10. The tool of claim 1, further comprising a coaxial introducer assembly removably disposed over a distal portion of the cannula assembly.

11. The tool of claim 1, further comprising a light source.

12. The tool of claim 1, wherein when the anti-rotation feature is displaced distally the decoupling bushing and the cannula assembly are both rotatable in the first direction and the second direction.

13. The rotation biopsy tool of claim 12, wherein the openable and closeable cavity closure is a door that translates vertically and pivot axially.

14. A method of obtaining a core tissue sample, comprising:
obtaining a core tissue sampling tool comprising:
a cannula assembly, the cannula assembly comprising:
an outer cannula;
an inner cannula coaxially disposed within the outer cannula, wherein a portion of the outer cannula is axially slidable relative to the inner cannula; and
a partoff tab coupled to the outer cannula; a trocar assembly;
a rotation member configured to rotate the cannula assembly in a first direction and the trocar assembly in the first direction and a second direction;
an anti-rotation feature configured to engage with a portion of the cannula assembly to prevent rotation of the cannula assembly in the second direction while permitting the rotation in the first direction;
a decoupling bushing comprising a circular flange having a nub extending distally from a distal face of the flange; and
a partoff tab actuation member,
wherein the inner cannula is fixedly coupled to the decoupling bushing, inserting a distal portion of the cannula assembly and the trocar assembly into an insertion;
positioning the distal portion of the cannula assembly and the trocar assembly adjacent an activating rotation of the cannula assembly and a portion of the trocar assembly in the first direction;
advancing the distal portion of the cannula assembly into the lesion, wherein the core tissue sample is disposed within the distal portion of the cannula assembly;
activating the partoff tab while the cannula assembly is rotating, wherein the core tissue sample is severed from the lesion by the partoff tab;
removing the distal portion of the cannula assembly from the insertion site;
ejecting the tissue sample from the cannula assembly; and
activating the portion of the trocar assembly to rotate in the second direction,
wherein a trocar of the trocar assembly is displaced distally to eject the core tissue sample from the cannula assembly, and
wherein the nub engages with the anti-rotation feature to restrict rotation of the decoupling bushing and the cannula assembly in the second direction while permitting the rotation in the first direction when the anti-rotation feature is displaced proximally as the core tissue sample is ejected from the core tissue sampling tool.

15. The method of claim 14, wherein the trocar is displaced proximally when the trocar assembly is rotated in the first direction.

16. The method of claim 14, further comprising illuminating the insertion site with a light source coupled to the core tissue sampling tool.

17. The method of claim 14, further comprising retaining the core tissue sample within the cannula assembly with the activated partoff tab when the distal portion of the cannula assembly is removed from the insertion site.

* * * * *